US007833917B2

(12) United States Patent
Shelley et al.

(10) Patent No.: US 7,833,917 B2
(45) Date of Patent: Nov. 16, 2010

(54) EXTENSIBLE AND STRETCH LAMINATES WITH COMPARABLY LOW CROSS-MACHINE DIRECTION TENSION AND METHODS OF MAKING SAME

(75) Inventors: Lindsay C. Shelley, Atlanta, GA (US); Thomas Brock, Woodstock, GA (US); Joy Francine Jordan, Marietta, GA (US); Renette Richard, Atlanta, GA (US); Christian Sanders, Decatur, GA (US); Eric Scott Kepner, Alpharetta, GA (US); Jared Lockwood Martin, Cumming, GA (US); Wing-Chak Ng, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1312 days.

(21) Appl. No.: 11/026,227

(22) Filed: Dec. 30, 2004

(65) Prior Publication Data
US 2006/0148354 A1  Jul. 6, 2006

(51) Int. Cl.
*B32B 27/04* (2006.01)
(52) U.S. Cl. ............... 442/149; 442/59; 442/328
(58) Field of Classification Search ............ 442/59, 442/149, 328
See application file for complete search history.

(56) References Cited
U.S. PATENT DOCUMENTS

| | | | |
|---|---|---|---|
| 3,338,992 A | 8/1967 | Kinney | |
| 3,341,394 A | 9/1967 | Kinney | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,153,751 A | 5/1979 | Schwarz | |

(Continued)

FOREIGN PATENT DOCUMENTS

EP  0650714 A1  5/1995

(Continued)

OTHER PUBLICATIONS

IST 70.4 (99), "Standard Test Method for Water Vapor Transmission Rate Through Non Woven and Plastic Film Using a Guard Film and Vapor Pressure Sensor", 1999.

(Continued)

*Primary Examiner*—D. Lawrence Tarazano
*Assistant Examiner*—Peter Y Choi
(74) *Attorney, Agent, or Firm*—Dority & Manning, P.A.

(57) ABSTRACT

A method of producing a laminate material includes the steps of providing a first flexible sheet material; providing a second flexible sheet material having a first surface and a second surface, and also having a first width of 1×; stretching the second flexible sheet material in a cross-machine direction to a second width of between about 1.2× and 3× when in a flattened state; necking the second flexible sheet material to produce an accordion shape, thereby reducing the second width of the sheet material to a third width, less than the width of the first width, such that the third width is between 0.65× to 0.975× when in an accordion shape; applying adhesive to the first surface of the second flexible sheet material with a slot coat adhesive process; and joining the first flexible sheet material to the first surface of the second flexible sheet material.

17 Claims, 9 Drawing Sheets

U.S. PATENT DOCUMENTS

| | | | |
|---|---|---|---|
| 4,340,563 | A | 7/1982 | Appel et al. |
| 4,795,668 | A | 1/1989 | Krueger et al. |
| 5,057,368 | A | 10/1991 | Largman et al. |
| 5,069,970 | A | 12/1991 | Largman et al. |
| 5,108,820 | A | 4/1992 | Kaneko et al. |
| 5,114,781 | A | 5/1992 | Morman |
| 5,116,662 | A | 5/1992 | Morman |
| 5,277,976 | A | 1/1994 | Hogle et al. |
| 5,336,552 | A | 8/1994 | Strack et al. |
| 5,382,400 | A | 1/1995 | Pike et al. |
| 5,423,935 | A * | 6/1995 | Benecke et al. ............ 156/291 |
| 5,466,410 | A | 11/1995 | Hills |
| 5,576,090 | A | 11/1996 | Suzuki |
| 5,683,787 | A | 11/1997 | Boich et al. |
| 5,914,084 | A | 6/1999 | Benson et al. |
| 6,039,906 | A * | 3/2000 | Sageser et al. ............ 264/156 |
| 6,114,263 | A * | 9/2000 | Benson et al. ............ 442/394 |
| 6,506,698 | B1 | 1/2003 | Quantrille et al. |
| 2002/0153086 | A1 | 10/2002 | Alper et al. |
| 2003/0183316 | A1 | 10/2003 | Hamulski |
| 2003/0207640 | A1 | 11/2003 | Anderson et al. |
| 2004/0121687 | A1 | 6/2004 | Morman et al. |
| 2005/0043460 | A1 | 2/2005 | McCormack et al. |

FOREIGN PATENT DOCUMENTS

| | | |
|---|---|---|
| EP | 1023363 B1 | 4/2004 |
| WO | WO 96/19346 | 6/1996 |
| WO | WO 01/09424 | 2/2001 |
| WO | WO 02/34511 | 5/2002 |
| WO | WO 03/040095 | 5/2003 |
| WO | WO 03/040442 | 5/2003 |
| WO | WO 2004/020174 | 3/2004 |
| WO | WO 2005/065947 | 7/2005 |

OTHER PUBLICATIONS

Manufacturers' Data Sheet, ExxonMobil LDPE, LD 202.48 Extrusion Coating Resin, ExxonMobil Chemical, Revised Apr. 2004.
"Opening Minds and Markets", Internet web page, http://www.dow.com/versify/, VERSIFY Plastomers and Elastomers, The Dow Chemical Company, viewed and printed Nov. 24, 2004, 5 pages.

* cited by examiner

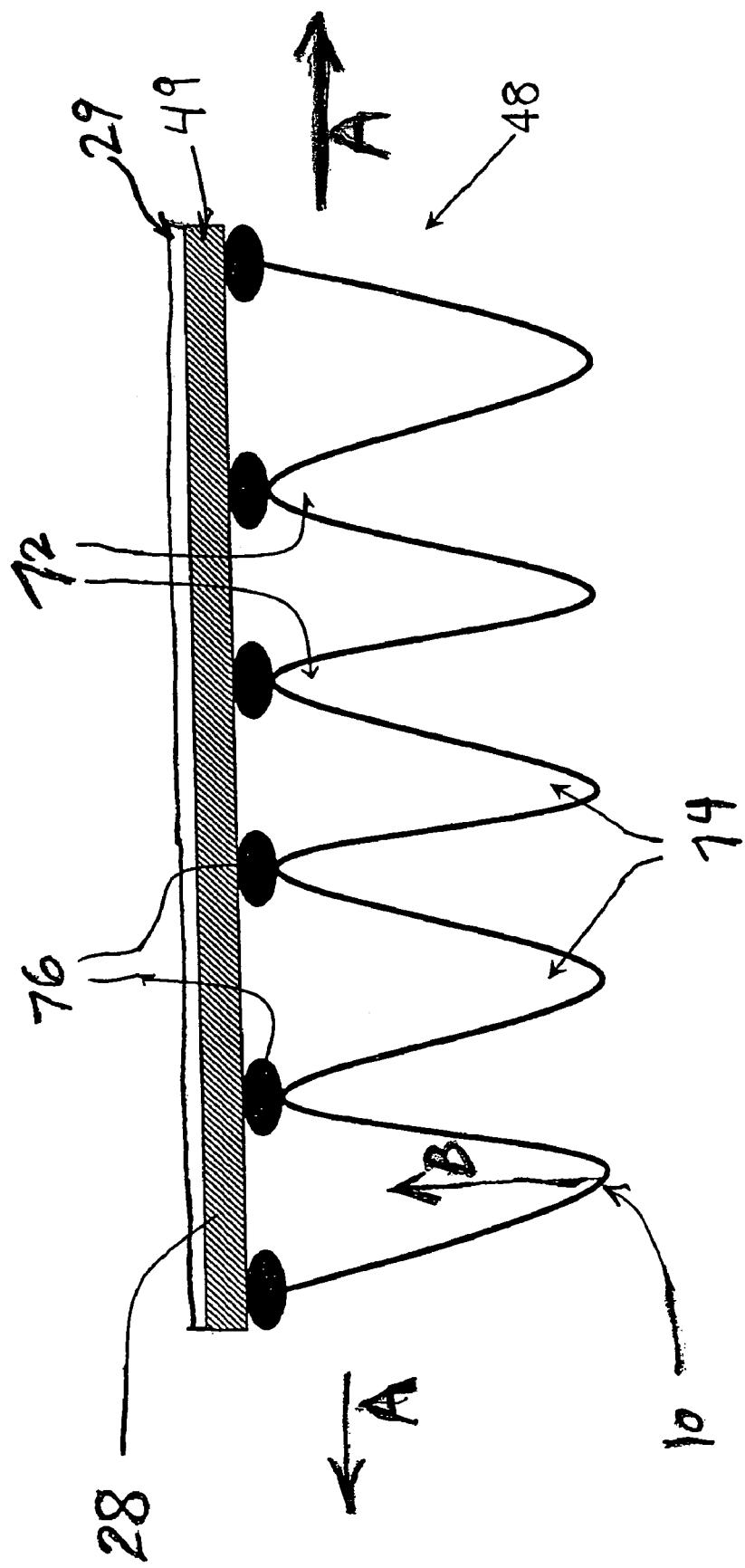

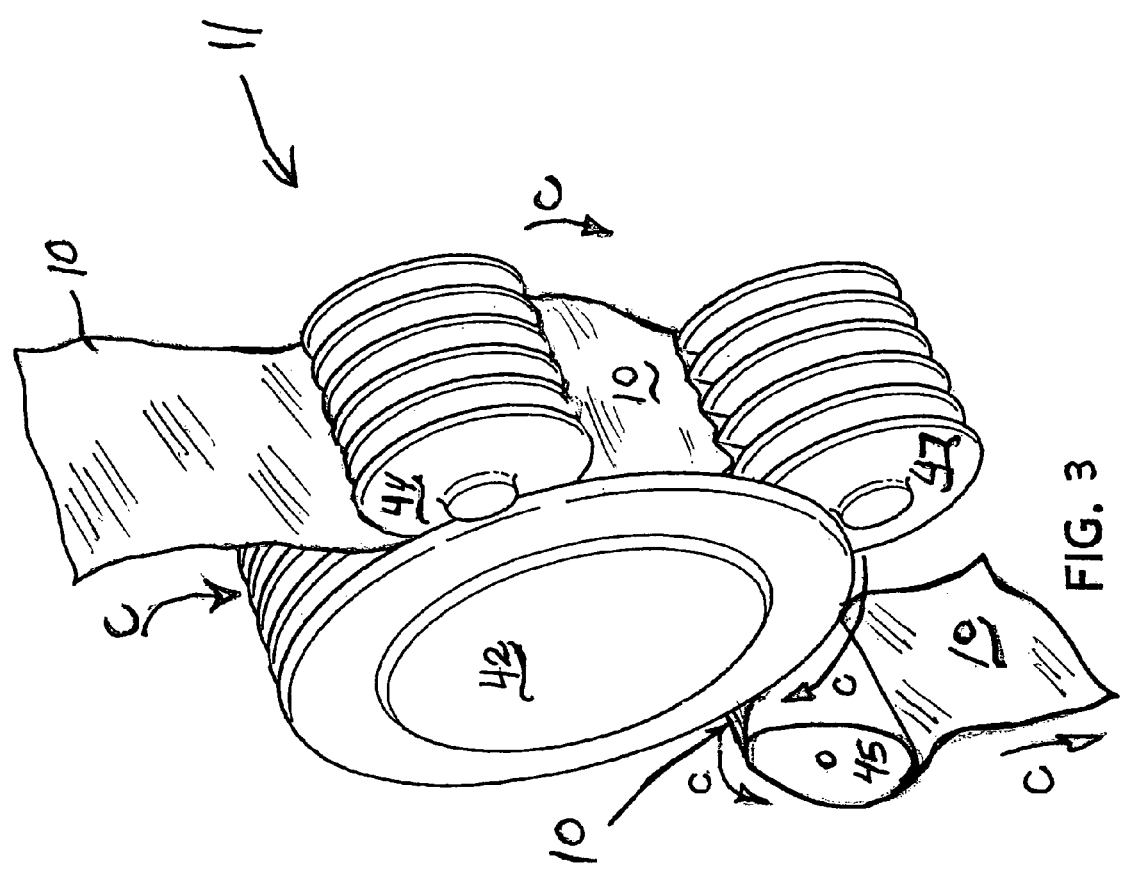

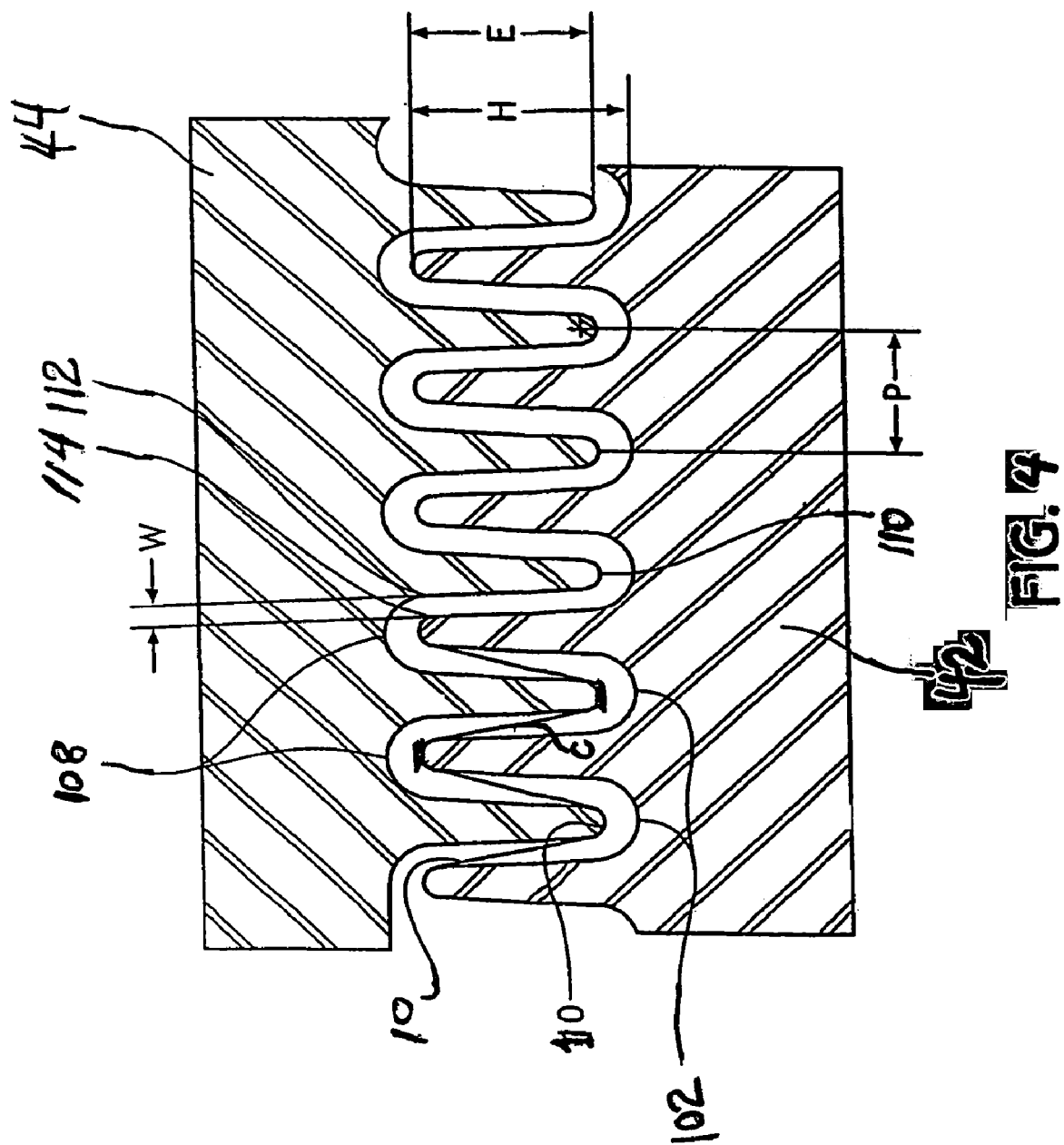

EXTENSIBLE AND STRETCH LAMINATES WITH COMPARABLY LOW CROSS-MACHINE DIRECTION TENSION AND METHODS OF MAKING SAME

FIELD OF THE INVENTION

The present invention relates to extensible and stretchable laminates, methods for making such extensible and stretchable laminates, and disposable product applications of such extensible and stretchable laminates. In particular, the present invention relates to film/nonwoven laminates that can be used to provide loft to personal care outercover materials, and that can also be used to provide ease of product donning and "fasten-anywhere" capability for hook and loop fastening systems.

BACKGROUND

Film and film/nonwoven laminates are used in a wide variety of applications, not the least of which is as outercovers/backsheets for limited use or disposable products including personal care absorbent articles such as diapers, training pants, swimwear, incontinence garments, feminine hygiene products, wound dressings, bandages and the like. The outercover or backsheet is the layer in a personal care article that is farthest from the skin of a consumer during product use. Film/nonwoven laminates also have applications in the protective cover area, such as in car, boat or other object cover components, tents. (outdoor recreational covers), and in the health care area in conjunction with such products as surgical drapes, hospital gowns and fenestration reinforcements. Additionally, such materials have applications in other apparel for clean room, health care, mortuary, veterinary, and other uses such as agricultural fabrics (row covers).

In the personal care area in particular, there has been an emphasis on the development of film laminates which have good barrier properties, especially with respect to liquids, as well as good aesthetic and tactile properties such as improved hand and feel. There has been an emphasis on addressing the "rubbery" or "plastic" feel encountered when touching polymeric sheet materials. There has been a further emphasis on the "stretch" comfort of such laminates, that is, the ability of the laminates to "give" as a result of the product utilizing such laminates being elongated in use.

Many such laminates used in consumer products are constructed with nonwoven facings which are necked (i.e., stretched in the machine direction and allowed to contract in the width or cross-machine direction) and laminated to an extensible or elastic film. The necking of the nonwoven facing provides the laminate with cross-machine direction extensibility. A greater degree of necking in the nonwoven facings results in greater extensibility in the finished laminate. However, these laminates are produced with relatively high cross-directional tension. Having relatively high cross-directional tension results in reduced ability to provide reliable fastening for a hook and loop type fastening system, when such laminates are to be used as the loop material for such a system. Further, having relatively high cross-directional tension results in reduced ability to provide good fit and gasketing, and makes donning of such products difficult, especially for younger consumers. Having high cross-directional tension also creates the impression that if such materials are stretched too much, they will rupture easily.

It has been found that in order to achieve low cross-machine tensions over a wider stretch, materials have to be necked beyond process capability. Additionally, such extreme necking results in material loss and increased production costs.

It would therefore be desirable to produce a laminate that has a higher level of extensibility at lower tensions across the length and width dimensions of the laminate. Such attribute could assist in providing fasten-anywhere capability to such a material, that is the ability of a hook to fasten anywhere across a laminate's width or length, and not just at a designated location. It would also be desired to provide a similar laminate with elasticity in multiple directions at relatively low tension levels. The present invention addresses these and other opportunities for improvement.

SUMMARY OF THE INVENTION

The present invention provides methods of producing a laminate material with comparably lower cross-machine direction tension, and the materials produced by the methods. The methods result in the production of fasten-anywhere loop material that can be used in a hook and loop fastening system, and with material that demonstrates a relatively soft feel and appearance. Additionally, the methods result in the production of material that ultimately leads to easier donning of personal care products. For the purposes of this application, the term "fasten-anywhere" shall mean that the material engages hooks on at least one of its surfaces, and desirably across much of the length and width dimensions of the material. Also for the purpose of this application, the term "donning" shall refer to the process of putting on a product about a consumer's legs and waist areas.

The methods of producing the materials are accomplished by taking into consideration a variety of factors, such as the level of necking of the facing material spacing between adhesive lines that bond the laminate, the types of polymers utilized in the film layer, the types of polymers used in the nonwoven facing layer, and type of adhesive application employed. Each of the factors can be used to enhance the loftiness and/or lower cross-machine direction tension of the laminate.

The spacing between adhesive lines is controlled by the amount of necking done to a laminate facing material following cross-directional stretching of the facing material, such as through a pair of intermeshed "grooved rolls", discs on axle apparatus, or through the use of a tenter frame, or similar apparatus. The drape attributes of the facing material can also be used to accentuate the placement/spacing of the adhesive lines.

In an alternative embodiment, by utilizing a film material as an elastic layer which incorporates a low density polyolefin having a density of less than about 0.89 g/cc, such film/nonwoven material laminate may demonstrate particularly low cross-machine direction tensions. In still another alternative embodiment, such low density polyolefin would have a density less than about 0.87 g/cc. In still another alternative embodiment, plastomer polyolefinic materials may be used in spunbond facing layers. In still a further alternative embodiment, a combination of adhesive technologies may be used either alone or in association with the previous methods to further reduce cross-machine direction tension values.

A method is specifically provided for producing a laminate material which includes the steps of providing a first flexible sheet material; providing a second flexible sheet material having a first surface and a second surface, and also having a first width of 1×; stretching the second flexible sheet material in a cross-machine direction to a second width of between about 1.2 and 3× when in a flattened state; necking the second flexible sheet material to produce an accordion shape, thereby reducing the second width of the sheet material to a third width, less than the width of the first width such that the third width is between 0.60× to 0.975× when in an accordion shape; applying adhesive to the first surface of the second flexible sheet material; and joining the first flexible sheet material to the first surface of the second flexible sheet material. In an alternative embodiment, the second flexible sheet material is stretched in the cross machine direction to a second width of between about 1.6× and 3×, or further alternatively, between about 2× and 3×. In another alternative embodiment of the inventive method, the second flexible sheet material is necked, reducing the width to a third width of between about 0.60× to 0.90×. The third width represents the width of the material while it is in an accordion-like configuration (as illustrated in FIG. 2). In a further alternative embodiment, such web is drawn between about 1.6× and 3.5× when stretched in the cross-machine direction. In one embodiment, such web is drawn between about 2.5× and 3.4×.

In another alternative embodiment of the method, the first flexible sheet material is a multilayered film. In still another embodiment of the method, the first flexible sheet material is a two-layered film with a skin layer positioned opposite to the second flexible sheet layer. In still another alternative embodiment of the method, the adhesive is applied to the second flexible sheet material using a slot coater adhesive system. In still a further alternative embodiment of the method, the first flexible sheet material is selected from the group consisting of an elongatable sheet and an elastic sheet. In yet another alternative embodiment of the inventive method the first flexible sheet is selected from the group consisting of a nonwoven web, a film and a foam sheet. In yet another alternative embodiment of the inventive method the first flexible sheet is an elastic sheet. In yet another alternative embodiment of the inventive method the elastic sheet comprises at least one styrenic block copolymer. In yet another alternative embodiment of the inventive method the second flexible sheet is selected from the group consisting of a woven and a nonwoven sheet. In still another alternative embodiment of the inventive method the second flexible sheet is a nonwoven sheet comprised of at least one polyolefin. In still another alternative embodiment of the inventive method, the second flexible sheet is a nonwoven sheet comprised of a blend of polypropylene and a propylene-ethylene copolymer. In still another alternative embodiment of the inventive method the second flexible sheet is a nonwoven sheet comprised of a 50/50 blend of polypropylene and a propylene-ethylene copolymer.

In still another alternative embodiment of the inventive method the second flexible sheet material is stretched in the cross-machine direction between about 2× and 3×. In still another alternative embodiment of the inventive method, the second flexible sheet material is necked between about 3 and 45 percent of its original width. In still another alternative embodiment of the inventive method the second flexible sheet material is necked between about 3 and 10 percent of its original width. In still another alternative embodiment of the inventive method the second flexible sheet material is necked between about 10 and 45 percent of its original width. In yet another alternative embodiment of the inventive method, the second flexible sheet material is necked such that said third width is between about 0.65× and 0.85×. In still another alternative embodiment of the inventive method, the second flexible sheet material is necked such that said third width is between about 0.90× and 0.975×. In still another alternative embodiment of the inventive method, the second flexible sheet material is necked such that said third width is between about 0.93× and 0.975×. In still another alternative embodiment of the inventive method, the method further includes an annealing step so as to cause retraction of the first flexible sheet material.

The invention also encompasses laminate material made by the method and any of the alternative embodiments. In one embodiment the produced laminate demonstrates a cross-machine direction tension between about 200 and 600 gf at 50 percent (as described below). In an alternative embodiment, the laminate demonstrates a cross-machine direction tension between about 200 and 450 gf at 50 percent.

In an alternative embodiment, such an inventive laminate material is either uniaxial or biaxial elastic and demonstrates a cross-machine direction tension between about 200 and 450 gf at 50 percent extension, with a machine direction tension between 500 and 1000 gf at 30 percent extension.

In still a further alternate embodiment, such an inventive laminate material of a first flexible layer and a second flexible layer is either uniaxial or biaxial elastic and demonstrates a cross-machine direction tension between about 200 and 750 gf at 50 percent extension, with a machine direction tension between 500 and 1000 gf at 30 percent extension.

In yet a further alternate embodiment, such an inventive laminate material of a first flexible layer and a second flexible layer is either uniaxial or biaxial elastic and demonstrates a cross-machine direction tension between about 200 and 450 gf at 50 percent extension, with a machine direction tension between 500 and 1000 gf at 30 percent extension.

The invention also encompasses a personal care article made with the laminate material made by the inventive process. The invention further encompasses a personal care article having an outercover, wherein the outercover comprises laminate material made by the inventive process.

BRIEF DESCRIPTION OF THE DRAWINGS

FIG. 2A is a representation of a cross-sectional view of an alternative embodiment of the laminate material of the present invention.

FIG. 3 is a representation of a perspective view of a grooved roll apparatus which may be used to stretch the nonwoven layer in accordance with the invention.

FIG. 4 is a detailed partial view of an engaged nip configuration of the grooved roll apparatus shown in FIG. 3.

DETAILED DESCRIPTION

Definitions

Figure 1:
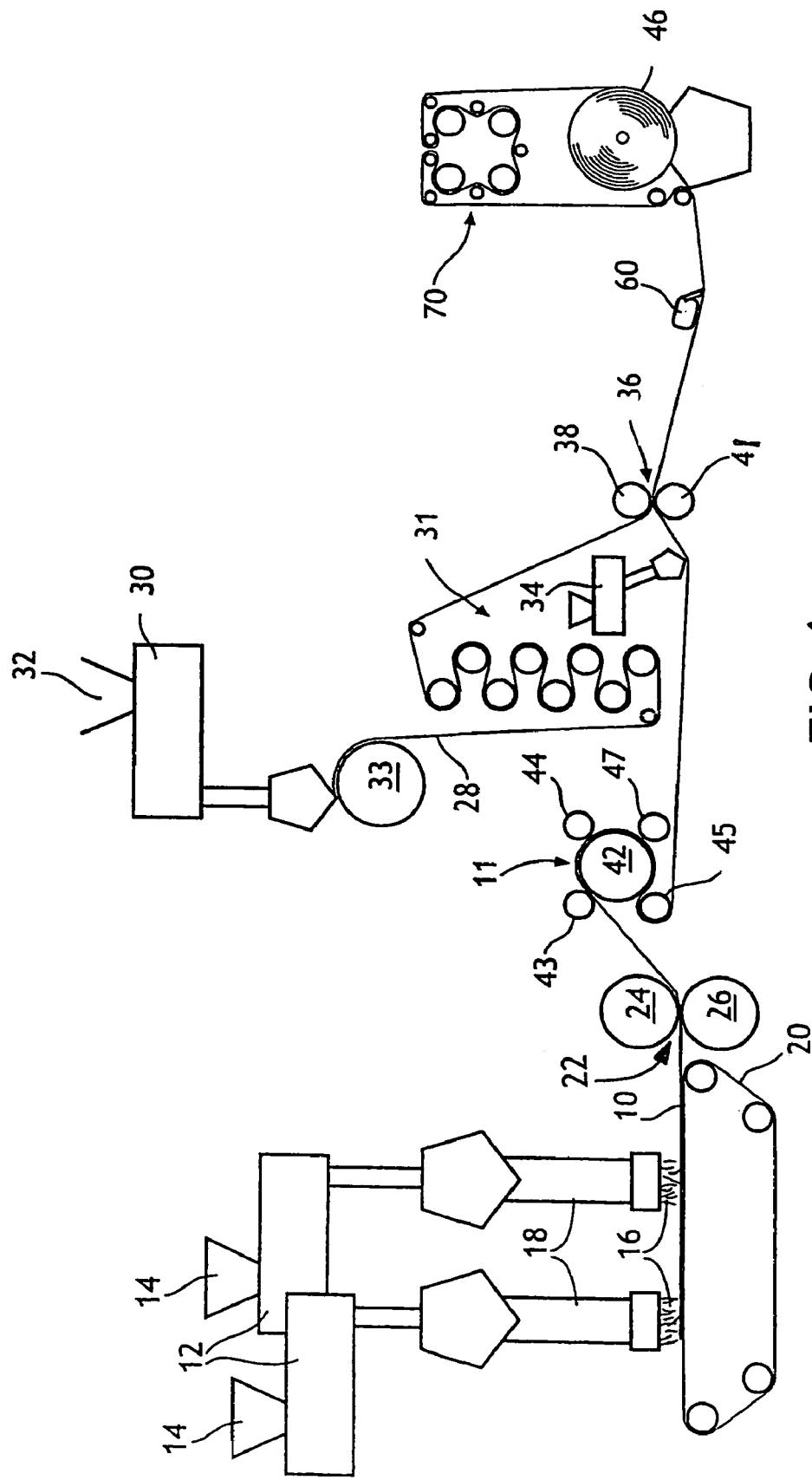
FIG. 1 is a schematic of an overall laminate process configuration incorporating the present invention.

The term "elastic" is used herein to mean any material which, upon application of a biasing force, is stretchable, that is, elongatable, to a stretched, biased length which is at least about 150 percent of its relaxed unbiased length, and which will recover at least 50 percent of its elongation upon release of the stretching, elongating force in less than one minute. A hypothetical example would be a one (1) inch sample of a material which is elongatable to at least 1.50 inches and which, upon being elongated to 1.50 inches and released, will recover to a length of not more than 1.25 inches in less than one minute. Many elastic materials may be stretched by much more than 50 percent of their relaxed length, for example, 80 percent or more, and many of these will recover to substantially their original relaxed length, for example, to within 105 percent of their original relaxed length, upon release of the stretching force.

As used herein, the terms "nonelastic" and "inelastic" shall be interchangeable and refer to any material which does not fall within the definition of "elastic," above.

As used herein, the term "recover" refers to a contraction (or retraction) of a stretched material upon termination of a biasing force following stretching of the material by application of the biasing force. For example, if a material having a relaxed, unbiased length of one (1) inch is elongated 50 percent by stretching to a length of one and one half (1.5) inches, the material would be elongated 50 percent (0.5 inch) and would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its one-half (0.5) inch elongation. Recovery may be expressed as [(maximum stretch length–final sample length)/(maximum stretch length–initial sample length)] times 100.

As used herein, the term "nonwoven web" means a web that has a structure of individual fibers or threads which are interlaid, but not in an identifiable, repeating manner. Nonwoven webs have been, in the past, formed by a variety of processes such as, for example, meltblowing processes, spunbonding processes and bonded carded web processes. Laminates containing such web materials may be formed and are considered a nonwoven material laminate.

As used herein, the term "microfibers" means small diameter fibers having an average diameter not greater than about 100 microns, for example, having a diameter of from about 0.5 microns to about 50 microns, more particularly, microfibers may have an average diameter of from about 4 microns to about 40 microns.

As used herein, the term "meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, the disclosure of which is hereby incorporated by reference.

As used herein, the terms "spunbonded fibers" and "spunbond fibers" shall be used interchangeably and shall refer to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or other well-known spunbonding mechanisms. The production of spunbonded nonwoven webs is illustrated in patents such as, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. No. 3,338,992 and 3,341,394 to Kinney, U.S. Pat. No. 3,542,615 to Dobo et al. The disclosures of these patents are hereby incorporated by reference.

As used herein, the term "bonded carded webs" refers to webs that are made from staple fibers which are usually purchased in bales. The bales are placed in a fiberizing unit/picker which separates the fibers. Next, the fibers are sent through a combining or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calendar rolls or ultrasonic bonding equipment is used to bond the fibers together, usually in a localized bond pattern through the web and/ or alternatively the web may be bonded across its entire surface if so desired. When using bicomponent staple fibers, through-air bonding equipment is, for many applications, especially advantageous.

As used herein, the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., and U.S. Pat. No. 5,336,552 to Strack et al. Conjugate fibers are also taught in U.S. Pat. No. 5,382,400 to Pike et al., and may be used to produce crimp in the fibers by using the differential rates of expansion and contraction of the two or more polymers. For two component fibers, the polymers may be present in varying desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

As used herein, the term "sheet" means a layer which may either be a film or a nonwoven web.

As used herein, the term "necked material" refers to any material which has been narrowed in at least one dimension by application of a tensioning force in another direction (dimension).

As used herein, the term "neckable material" means any material which can be necked.

As used herein, the term "percent neckdown" or "necked" refers to the ratio determined by measuring the difference between the un-necked dimension and the necked dimension of the neckable material and then dividing that difference by the un-necked dimension of the neckable material, the quotient multiplied by a 100.

"Neck bonding" refers to the process wherein an elastic member is bonded to a second member (facing) while only the second member (facing) is extended or necked so as to reduce its dimension in the direction orthogonal to the extension. Such materials generally have cross-machine direction stretch.

As used herein, the terms "elastic necked-bonded material" or "neck-bonded laminate" shall be used interchangeably and refer to a laminate material having an elastic sheet joined to a necked material at least at two places. The elastic sheet may be joined to the necked material at intermittent points or may be completely bonded thereto. The joining is accomplished while the elastic sheet and the necked material are in juxtaposed configuration. The elastic necked-bonded material is elastic in a direction generally parallel to the direction of neckdown of the necked material and may be stretched in that direction to the breaking point of the necked material. An elastic necked bonded material may include more than two layers. For example, the elastic sheet may have necked material joined to both of its sides so that a three-layer composite or laminate of elastic necked—bonded material is formed having a structure of necked material/elastic sheet/necked material. Additional elastic sheets and/or necked material layers may be added. Yet other combinations of elastic sheets and necked materials may be used. For example, an elastic sheet of a multilayered film may be utilized, such as for example a film with a relatively thicker layer and a relatively thinner skin layer.

The terms "elongatable" and "extensible" shall be used interchangeably and shall describe the ability of a material to extend without rupture in one direction (such as by about 10 percent from a starting length, or desirably in one embodiment greater than about 50 percent), but not necessarily including the ability to recover once extended.

"Neck-stretch bonding" generally refers to a process wherein an elastic member is bonded to another member while the elastic member is extended, such as by at least about 25 percent of its relaxed length and the other layer is a necked, non-elastic or elongatable layer. "Neck-stretch bonded laminate" refers to a composite elastic material made according to the neck-stretch bonding process, i.e., the layers are joined together when both layers are in an extended condition and then allowed to relax. Such laminates usually have multi or omni-directional stretch properties. Neck stretch bonded laminates are described in U.S. Pat. Nos. 5,116,662 and 5,114,781 each incorporated by reference hereto in its entirety.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the terms "machine direction" or MD means the direction along the length of a fabric (such as a woven or nonwoven material) or film in the direction in which it is produced. The terms "cross machine direction," "cross directional," or CD mean the direction across the width of fabric or film, i.e. a direction generally perpendicular to the MD.

The basis weight of nonwoven fabrics or films is usually expressed in ounces of material per square yard (osy) or grams per square meter (g/m$^2$ or gsm) and the fiber diameters useful are usually expressed in microns. (Note that to convert from osy to gsm, multiply osy by 33.91). Film thicknesses may also be expressed in microns or mil.

As used herein the term "set" refers to retained elongation in a material sample following the elongation and recovery, i.e. after the material has been stretched and allowed to relax.

As used herein the term "percent set" is the measure of the amount of the material stretched from its original length after being cycled. The remaining strain after the removal of the applied stress is measured as the percent set. The percent set can be described as that location on a graph where the retraction curve of a cycle crosses the elongation axis, and as further discussed below, and is represented by the following formula:

$$\frac{\text{Final length} - \text{Initial length}}{\text{Stretched length} - \text{Initial length}} \times 100$$

As used herein, a "stretching apparatus" shall refer to at least one pair of intermeshing grooved rolls, intermeshing discs on parallel axles (also referred to disc on axle arrangements), belt arrangements or tenter frames, which allow for the stretching of a material in either the cross-machine direction or machine direction. In operation, the grooved rolls or discs intermesh to provide material stretch at multiple points across a single direction of a material. Alternatively, such stretching apparatus may include a series of sets of intermeshing grooved rolls or intermeshing discs on axles, or a main grooved roll and a series of satellite grooved rolls positioned about the main grooved roll. Examples of such stretching apparatus may be found in U.S. Pat. No. 4,153,751 to Schwarz, Application WO2004/020174 for Device and Process for Treating Flexible Web By Stretching Between Intermeshing Forming Surfaces to Robert Gerndt et al., filed Aug. 22, 2003, and U.S. application Ser. No. 10/881,064 to Michael T. Morman, for Efficient Necked Bonded Laminates and Methods of Making Same, filed Jun. 30, 2004, each incorporated by reference in its entirety.

As used herein and in the claims, the term "comprising" is inclusive or open-ended and does not exclude additional unrecited elements, compositional components, or method steps. Accordingly, such terms are intended to be synonymous with the words "has", "have", "having", "includes", "including", and any derivatives of these words.

For the purposes of this application, values of load loss and other "elastomeric functionality testing" have been generally measured in the CD direction, unless otherwise noted. Unless otherwise noted, such test values have been measured at the 30 or 50 percent elongation point of a 101 percent total elongation cycle.

In calculating CD tensions, the "load loss" test may be utilized by first elongating a sample to a defined elongation in a particular direction (such as the CD) of a given percentage (such as 70, or 101 percent as indicated) and then allowing the sample to retract to an amount where the amount of resistance is zero. The load loss may be calculated at a given elongation, such as at the 50 percent elongation. Unless otherwise indicated, the value was read at the 50% elongation level (on a 101 percent elongation test) and then used in the calculation. For the purposes of this application, the load loss was calculated as follows. Up values were taken during extension and down values during retraction.

$$\frac{\text{Cycle 1 extension tension (at 50\% elongation)} - \text{cycle 2 retraction tension (at 50\% elongation)}}{\text{Cycle 1 extension tension (at 50\% elongation)}} \times 100$$

For the test results reflected in this application, the defined elongation was 101 percent unless otherwise noted. The actual test method for determining load loss values is described below. The tension at the first cycle extension at 50 percent elongation (in CD) is called for the purposes of the examples, CD tension at 50%, whereas the tension at the first cycle at 30 percent elongation (in MD) is called for the purposes of the examples MD tension at 30%. These measured tension values are derived from the test method/apparatus below.

Test Method Procedures

Cycle Testing:

The materials were tested using a cyclical testing procedure to determine load loss, tensions in various directions and percent set. In particular, cycle testing was utilized to 101 percent defined elongation. For this test, the sample size was 3 inch in the MD by 7 inch in the CD (for CD testing) and 3 inch in the CD and 7 inch in the MD (for MD testing). The grip size was 3 inch width. The grip separation was 4 inch. The samples were loaded such that the cross-direction or machine direction of the sample was in the vertical direction as stipulated. A preload of approximately 10-15 grams was set. The test pulled the sample at 20 inches/min (500 mm/min) to 101 percent elongation (4.04 inches in addition to the 4 inch gap), and then immediately (without pause) returned to the zero point (the 4 inch gauge separation). The test repeated the cycle up to 5 times and values at 30% or 50% taken (CD tensions were taken at 50% and MD tensions were taken at 30%). Testing (resulting in the data in this application) was done as a 2 cycle test following material removal from production equipment. The results of the test data are from the first cycle. The testing was done on a Sintech Corp. constant rate of extension tester 2/S with a Renew MTS mongoose box (controller) using TESTWORKS 4.08b software. (Sintech Corp, of Cary, N.C.). The tests were conducted under ambient conditions. This test was used to determine tension levels of laminates at specific elongations (strain).

Water Vapor Transmission Rate (WVTR)/ Breathability:

A suitable technique for determining the WVTR (water vapor transmission rate) value of a film or laminate material of the invention is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow which is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. This information is used to calculate the transmission rate at which moisture is transmitted through the test material according to the equation:

$$TR^{-1}_{test\ material} = TR^{-1}_{test\ material,\ guardfilm,\ airgap} - TR^{-1}_{guardfilm,\ airgap}$$

Calculations:

WVTR: The calculation of the WVTR uses the formula:

$$WVTR = F\rho_{sat}(T)RH/(A\rho_{sat}(T)(1-RH))$$

where:
F=The flow of water vapor in cc/min.,
$\rho_{sat}(T)$=The density of water in saturated air at temperature T,
RH=The relative humidity at specified locations in the cell,
A=The cross sectional area of the cell, and,
$\rho_{sat}(T)$=The saturation vapor pressure of water vapor at temperature T.

For the purposes of this Application, the testing temperature for the above test was at about 37.8° C., the flow was at 100 cc/min, and the relative humidity was at 60%. Additionally, the value for n was equal to 6 and the number of cycles was 3.

Strip Tensile Test to produce stress/strain curve

This method tests for strip tensile, energy and percent (%) stretch on a 3×6 inch (76×152 mm) piece of nonwoven material. The strip tensile test is a tension test where the entire specimen width is gripped in the jaws, having a gage length of 3 inches. The grip size is 3 inches. Tensile is the maximum load (peak load) before the specimen ruptures. Energy is the area under the load-elongation curve from the origin to the point of rupture. Percent stretch is the increase in the length produced in the gage length expressed as a percentage. The samples were loaded such that the cross-direction of the samples was in the vertical direction. The test pulls the sample at 12 inches/min (300 mm/min) until the sample breaks. The testing was done on a Sintech Corp. constant rate of extension tester 2/S with a Renew MTS mongoose box (controller) using TESTWORKS 4.08b software. (Sintech Corp., of Cary, N.C.) The tests were conducted under ambient conditions. This test was used to evaluate tension, for example load vs. strain data for nonwoven facing layers (as opposed to laminates). The test also provides data for peak load, and peak elongation at the peak load (see FIG. 10).

The present invention relates to the formation of a laminate from at least two flexible sheet materials. The flexible sheet materials are such that when used in a laminate will provide the desired barrier, aesthetic appearance, tactile feel, extensibility (tension) and engageability properties. Desirably, in one embodiment, the laminate includes two flexible sheet materials, with one of the flexible sheet materials acting as a facing material (or facing layer) and the other acting as an extensible or elastic liquid barrier layer. The facing material layer of the laminate is designed as the outermost layer of a personal care article (the layer of the outercover or backsheet facing away from the skin of a consumer), to provide a pleasant tactile feel and fasten anywhere capability to the outercover, whereas the barrier layer is designed to provide a liquid barrier to product applications such as outercovers and containment flaps. The barrier layer is the layer of the laminate that is closest to the wearer's skin in the outercover application.

One category of such flexible sheet materials to be used as facing layers are nonwoven webs. Nonwoven web materials suitable for use in the method of this invention may be, for example, selected from the group consisting of spunbond, meltblown, spunbond-meltblown-spunbond laminates, coform, spunbond-film-spunbond laminates, bicomponent spunbond, bicomponent meltblown, biconstituent spunbond, biconstituent meltblown, bonded carded webs, airlaid webs, and combinations thereof.

The nonwoven web materials are desirably formed with polymers selected from the group including polyolefins, polyamides, polyesters, polycarbonates, polystyrenes, thermoplastic elastomers, fluoropolymers, vinyl polymers, and blends and copolymers thereof. Suitable polyolefins include, but are not limited to, polyethylene, polypropylene, polybutylene, and the like; suitable polyamides include, but are not limited to, nylon 6, nylon 6/6, nylon 10, nylon 12 and the like; and suitable polyesters include, but are not limited to, polyethylene terephthalate, polybutylene terephthalate and the like. Particularly suitable polymers for use in the present invention are polyolefins including polyethylene, for example, linear low density polyethylene, low density polyethylene, medium density polyethylene, high density polyethylene and blends thereof; polypropylene; polybutylene and copolymers as well as blends thereof. Additionally, the suitable fiber forming polymers may be of polyolefinic elastomers (or plastomers demonstrating both elastomeric and plastic polymer properties) or may be of polyolefins and polyolefinic elastomers blended therein. Such suitable web forming polymer materials include single site catalyzed polyolefins, such as metallocene catalyzed polyolefins and constrained geometry catalyzed polyolefins. Desirably such single site catalyzed polyolefin materials demonstrate stretch and recovery properties and have a density of less than about 0.89 g/cc. In a further embodiment, such single site catalyzed materials have a density less than about 0.87 g/cc. Such single-site catalyzed polymers include AFFINITY™ plastomers from The Dow Chemical Company and EXACT™ polymers from Exxon Mobil. Additionally, in one alternative embodiment, such nonwoven material is formed from a blend of a nonelastic polyolefin and a different elastomeric polyolefin material. For example, in one embodiment, such nonwoven material is a spunbond web formed from a blend of polypropylene and a propylene copolymer. The propylene copolymer will preferably comprise at least about 50 weight percent of units derived from propylene and at least about 5 weight percent of units derived from a comonomer other than propylene, the copolymer characterized as having a crystallinity index as measured by X-ray diffraction of less than about 40%. The comonomer is typically one or more of ethylene (a preferred comonomer), a $C_{4-20}$ α-olefin, a $C_{4-20}$ diene, a styrenic compound, and the like. Preferred propylene copolymers can be further characterized as having at least one of the following properties: (i) $^{13}C$ NMR peaks corresponding to a regio-error at about 14.6 and about 15.7 ppm, the peaks of about equal intensity, (ii) a DSC curve with a $T_{me}$ that remains essentially the same and a $T_{max}$ that decreases as the amount of comonomer, i.e., the units derived from ethylene and/or the unsaturated comonomer(s), in the copolymer is increased. The preferred copolymers of this embodiment are characterized by at least one, preferably both of these properties. In other embodiments of this invention, these copolymers are characterized further as also having a skewness index, $S_{ix}$, greater than about −1.20. Each of these properties and their respective measurements are described in detail in WO2003/040442 which is incorporated herein by reference.

The propylene copolymers of this invention can be made by any process, and include copolymers made by Zeigler-Natta, CGC, metallocene, and nonmetallocene, metal-centered, heteroaryl ligand catalysis. These copolymers include random, block and graft copolymers. The copolymers may also include copolymers such as those disclosed in WO2003/040095 (which is hereby incorporated by reference in its entirety), where the comonomer (ethylene) is incorporated in an alternating fashion.

The copolymer component of the blend desirably demonstrates a melt flow rate of between 2 and 25 g/10 min, demonstrates a density of between about 0.858 and 0.888, demonstrates a narrow molecular weight distribution of between 2 to 3, and has a comonomer content of between 5 and 15 percent. Desirably, in one embodiment, the nonelastic polyolefin component of such a blend is present in a percentage of between about 45 and 85 percent, while the copolymer portion of the blend is present in a percentage of between about 15 and 55. In one embodiment, such polymers are present in about a 50/50 ratio within the fibers of the nonwoven facing layer. Such polymers are present in a blend throughout the homofilaments of the facing layer, as opposed to co-continuous phases of bicomponent fibers.

In an alternative embodiment, such nonwoven facing sheet includes electrostatically charged fibers such as electrostatically charged polyolefin fibers. It has been found that electrostatic treatment of fibers tends to increase the machine direction orientation of fibers, and thereby decreases cross-machine direction fiber orientation. The result is that cross-machine extension loads are decreased versus the same nonwoven sheet comprised of fibers that are not electrostatically charged prior to webforming. Moreover, the increased machine direction fiber orientation improves nonwoven sheet drape in the cross-machine direction, which in some embodiments may be advantageous, in order to increase peel strength.

Nonwoven fabrics which are used in such laminates, prior to conversion into such laminates, desirably have a basis weight between about 10 g/m² and 50 g/m² and even more desirably between about 12 g/m² and 25 g/m². In an alternative embodiment, such nonwoven fabrics have a basis weight between about 15 g/m² and 20 g/m². In addition to use of nonwoven layers as facing layers, woven layers may also be used, with basis weights similar to those described above for nonwoven materials.

Categories of flexible sheet materials which can be used in such laminates as barrier layers, include polymeric films and foam sheets. Such polymeric films and foam sheets provide a barrier to fluids while remaining flexible and can be apertured, slit, filled, monolithic, breathable, extensible, stretchable or combinations thereof. Examples of such films are described in WO 96/19346, to McCormack et al., incorporated herein by reference in its entirety. Other examples of such films may be found in U.S. application Ser. No. 10/703,761, filed Nov. 7, 2003 and is hereby incorporated by reference herein in its entirety. Examples of foam materials include closed cell foams, such as polyurethane foams. Such barrier layers are desirably extensible/elongatable, and even more desirably, elastic. In one embodiment, such barrier layers are uniaxially extensible or elastic. In another alternative embodiment, such barrier layers are biaxially extensible or elastic. The laminates made from such facing layers and barrier layers are desirably in one embodiment, uniaxially extensible or elastic, and in an alternative embodiment, biaxially extensible or elastic.

Various thermoplastic elastomers or plastomers are contemplated for use in this invention as the barrier layer. However, thermoplastic block polymers such as styrenic block copolymers are examples of useful elastic polymers of the invention. Specific examples of useful styrenic block copolymers include hydrogenated polyisoprene polymers such as styrene-ethylenepropylene-styrene (SEPS), styrene-ethylenepropylene-styrene-ethylenepropylene (SEPSEP), hydrogenated polybutadiene polymers such as styrene-ethylenebutylene-styrene (SEBS), styrene-ethylenebutylene-styrene-ethylenebutylene (SEBSEB), styrene-butadiene-styrene (SBS), styrene-isoprene-styrene (SIS), and hydrogenated poly-isoprene/butadiene polymer such as styrene-ethylene-ethylenepropylene-styrene (SEEPS). Polymer block configurations such as diblock, triblock, multiblock, star and radial are also contemplated in this invention. In some instances, higher molecular weight block copolymers may be desirable. Block copolymers are available from Kraton Polymers U.S. LLC of Houston, Tex. under the designations Kraton D or G polymers, and Septon Company of America, Pasadena, Tex. under the designations Septon 2004, Septon 4030, and Septon 4033. Another potential supplier of such polymers includes Dynasol of Spain. In particular, Septon 2004 SEPS triblock polymer is particularly suitable for the invention. Blends of such elastomeric materials are also contemplated as the "elastomeric component". In one embodiment, it is desirable that the styrenic block copolymer is a SEPS polymer. The thermoplastic elastomers themselves may include processing aids and/or tackifiers associated with the elastomeric polymers. Other thermoplastic elastomers useful in the invention include olefinic-based elastomers such as EP rubber, ethyl, propyl, butyl terpolymers, block and copolymers thereof. Still further alternative examples of useful elastomeric materials include single site catalyzed materials such as those previously described with reference to the first flexible facing layer. Such single site catalyzed materials may be for example, low density polyethylene's having densities lower than about 0.89 g/cc. Additionally, in still another alternative embodiment, the barrier layer may be constructed of multiple layers with elastic properties. An example of such may include a styrenic block copolymer layer and a low density polyethylene layer.

In a further alternative embodiment, such barrier layer is breathable. In yet a further alternative embodiment, such barrier layer is filled elastic films including a thermoplastic elastomer polymer and a filled semi crystalline predominantly linear polymer. The film includes between about 25 and 70 weight percent filler, between about 5 and 30 by weight percent semi-crystalline linear polymer, and between about 15 and 60 by weight elastomeric polymer. The filler is closely associated with the semi-crystalline linear polymer and the laminate demonstrates a breathability of greater than 100 g/m$^2$/24 hours, desirably greater than 1000 g/m$^2$/24 hours.

While it should be recognized that flexible sheet materials can be chosen from a broad spectrum of materials, polymeric films (for the first flexible sheet material) and nonwoven webs (for the second flexible sheet material) are described hereunder for illustrative purposes. The inventive method for producing the laminate involves adhesively laminating to a first flexible barrier layer, a cross-machine direction stretched, and subsequently necked second flexible layer.

FIG. 1 is a schematic illustration of a laminating process of the present invention. Specifically, FIG. 1 illustrates a process for laminating a nonwoven web to an elastic film. As shown, a nonwoven web 10 is formed by feeding extruders 12 from polymer hoppers 14 and forming continuous filaments 16 from filament formers 18 onto web former 20. The resulting web 10 is bonded at calender nip 22 formed by a patterned roll 24 and anvil roll 26, one or both of which may be heated to a thermal bonding temperature. Alternatively, such web or webs may be compacted by compaction rolls (not shown) rather than bonding rolls. After bonding, web 10 is stretched in accordance with the invention using any number of stretching technology methods. For the purposes of illustration, the stretching is accomplished by a satellite groove roll stretching unit 11 having grooved anvil roll 42 and satellite rolls 43, 44, 47, 45 and an adhesive is applied to the web at adhesive station 34. It should be appreciated that the groove stretching in the cross-machine direction may be alternatively done with the use of a single pair of grooved rolls or a series of grooved rolls. In a further alternative embodiment, such stretching may be accomplished by a disc on axle apparatus as described in U.S. application Ser. No. 10/881,064 to Michael T. Morman, for Efficient Necked Bonded Laminates and Methods of Making Same, filed Jun. 30, 2004, or one or more tenter frames. The apparatus and process for stretching will be described below in further detail with reference to FIGS. 3 and 4.

Film 28 is formed by feeding extruder 30 from polymer hopper 32 and casting onto chill roll 33. The film 28 is stretched by a machine direction orienter (MDO) 31 and the film and nonwoven web are combined at nip 36 between rolls 38, 41 maintained at a desired adhesive bonding temperature. The laminate is then directed to a slitter 60, if slitting is desired, and to temperature controlled section 70 to anneal and/or retract and chill as desired. Finally, the laminate is directed to winder 46 or, optionally, directed to further processing.

It is particularly desirable, for the purposes of the invention, to neck the nonwoven material (such as the spunbond described) following stretching of the web in the cross-machine direction. Specifically, it is desirable to start with a nonwoven facing of a given cross-machine direction width. The "given" cross-directional width will be referred to in this application as the "original" width and describe the width immediately following web formation or web unwind (if provided from a pre-formed roll). For the purposes of this application, the original width is designated as x (or 1x).

The nonwoven facing layer is then desirably stretched in the cross-machine direction such that the stretched width (second width) is between about 1.2× and 3× in a flattened state. Alternatively, such nonwoven web is stretched in the CD such that it demonstrates a second width of between about 1.6× and 3× in a flattened state. Still, alternatively, such nonwoven facing layer is stretched in the cross-machine direction such that its second width is between about 2.0× and 3.0× in a flattened state. In a further alternative embodiment, such nonwoven facing layer is stretched in the cross-machine direction such that its second width is between about 2.0× and 2.75×. In still a further alternative embodiment, the cross-machine width following stretching is between about 2.0× and 2.5×.

For example, if the original width is 100 cm, it is desirable to stretch the nonwoven facing layer such that its second width is between about 120 and 300 cm, or alternatively between about 200-300 cm. In an alternative embodiment, it is desirable to stretch the nonwoven facing layer such that its second width is between about 200 to 275 cm. In still a further alternative embodiment, the second width is between about 200 to 250 cm. Desirably, such stretching is achieved by intermeshing grooved rolls as described below.

It is desirable in one embodiment for the grooved rolls to draw the nonwoven web in the CD direction to between about 1.6× and 3.5×. In still another alternative embodiment, it is desirable for the grooved rolls to draw the nonwoven web to between about 2.5 and 3.4×.

In order to calculate potential draw of the material using the grooved roll apparatus, the potential stretch dimension (such as length) is divided by the original dimension (such as length). If a hypothetical triangle is envisioned wherein the two adjacent peaks of a grooved roll form two of the points and the engagement between the peaks of the different rolls forms the third point of the triangle, the original length may be designated as "P", as the distance between the two adjacent peak points (as seen in FIG. 4). The distance from the peak (highest point) to the bottom of the engagement peak (lowest point) may be designated as "c" and the depth of engagement may be designated as "E". The stretch length would then be "2c", where "c" is the hypotenuse of the right triangle formed from the length P/2, E, and c and, where:

$$c = ((P/2)^2 + E^2)^{1/2} \text{ so the draw may be expressed by the following equation:}$$

$$\text{Draw} = \frac{2 * ((P/2)^2 + E^2)^{1/2}}{P}$$

If "P" is equal to 0.125 inches and E is equal to 0.20 inches, the draw would be equal to 3.35. If the penetration was only 0.15 inches instead of 0.20 inches, the draw would be 2.6.

Figure 2:
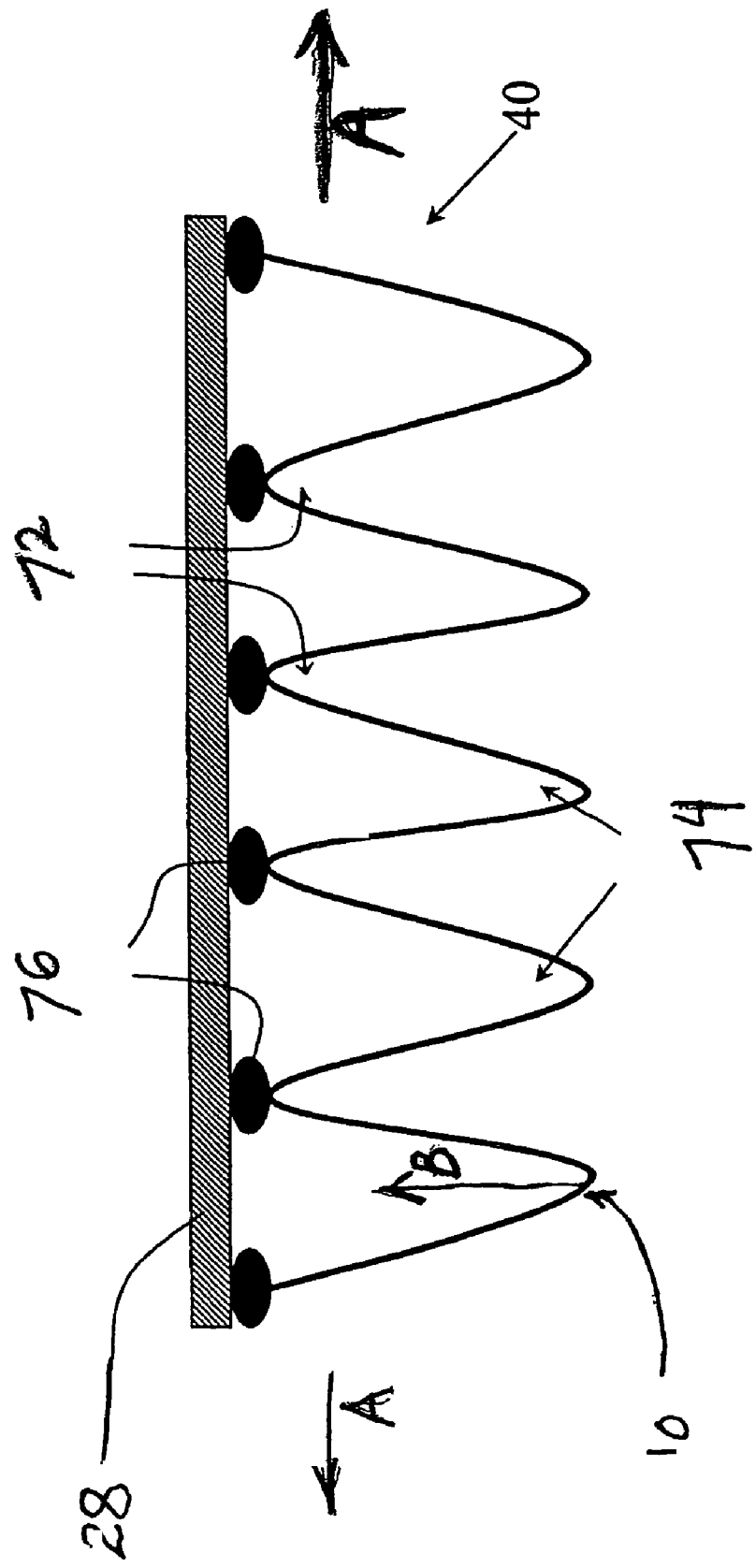
FIG. 2 is a representation of a cross-sectional view of the laminate material of the present invention.

Following stretching, the facing layer is necked such that it reduces its width dimension (to a third width) to between about 0.60× to 0.975× to produce an accordion-shaped material as illustrated in FIG. 2. In effect, the produced accordion then has the width narrower than the original width, if in an unflattened state (accordion shape) but has a cross-directional width greater than the original width, if measured in a flattened state.

In one additional embodiment, it is desirable to have a cross-directional third width of between about 0.90× to 0.975× (in accordion state). In a further additional embodiment, it is desirable to have a cross-directional third width of between about 0.93× and 0.975×. If a blend of both traditional polyolefin and propylene ethylene copolymers is used, it is desirable for the third width to be between about 0.60× and 0.90×, alternatively between about 0.65× and 0.85×. As previously stated, such measurement is taken while the web is in an accordion shape. If overnecking occurs, the peaks in the accordion-like material would be spaced too closely together on the laminated film, resulting in reduction in the film's ability in the final laminate to stretch (as will be described further below). Such necking may be accomplished by a pair or series of necking rolls (not shown), that is, rolls which are operating at faster speeds than the proceeding processing step so as to narrow the width of the web in the cross-machine direction. Alternatively, such necking may be accomplished by the lamination rolls themselves 38,41, which likewise may be operated at faster speeds than the last grooved roll nip 45, 42. In an alternative embodiment, the last grooved roll (such as 45) in a series of satellite rolls may be replaced with a smooth rubber roll to accentuate the necking effect between it and the lamination nip 36. This is illustrated in FIG. 3 as 45.

FIG. 1 illustrates a process where both the film layer (first flexible layer) and the nonwoven are (second flexible layer) are produced in-line with the remainder of the laminating process. Alternatively, the film and/or the nonwoven may be provided to the laminating process as pre-formed material rolls (not shown).

FIG. 2 is a stylized representation of a cross-sectional view of the material laminate 40 produced by the inventive method as illustrated in FIG. 1. When the flexible sheet material 10 is stretched by the satellite groove roll stretching unit 11, the corrugated surface of the flexible sheet material 10 will be made up of a series of alternating surface contacting peaks 72 and recessed troughs 74 between the peaks 72. Ideally, the facing layer material 10 will be attached to the other sheet material 28 (such as a single layer film) with the adhesive 76 only at the discrete points where the peaks 72 of the facing layer sheet material 10 contact the film (or other material as noted) 28. It is desirable for the space between adhesive points to be such that the film has room to stretch. If the peaks and resulting bond points are too closely spaced, or bond points are wide, the film will have limited stretch and will likely demonstrate higher tension levels in the cross-machine direction. If the appropriate space is provided (resulting from the necking level described), the film will first stretch upon application of a biasing force in the cross-machine direction, and then the peaks and troughs will provide additional room for stretch upon application of additional biasing force. If the nonwoven facing layer is made of somewhat extensible or elastic polymeric materials, the nonwoven facing layer will have even more give to allow the film to stretch further in the directions "A". The peaks will decrease in height from the flexible layer 28, in the direction "B".

As can be seen in FIG. 2A, an alternative embodiment of the processed laminate 48 is illustrated in which the flexible layer 28 is comprised of a multilayer film. Specifically, the film includes a skin-like layer 29 (a layer significantly thinner than the other film layer 49). Desirably, such skin-like layer is on a side of the laminate that is opposite to that of the facing layer. Such skin layer may be made of polyolefin materials, and may be advantageous as providing a tack-barrier for the film.

The groove roll arrangement of the inventive method may be single rolls immediately adjacent one another such that the peaks of one roll lie in the valleys of an adjacent roll (as previously described), or alternatively, they be a single or main anvil roll that is encircled by smaller satellite rolls. For instance, in one embodiment, the nonwoven support layer or laminate may be coursed through a grooved roll arrangement in which a main anvil roll is encircled by one or more satellite rolls. Such an arrangement is illustrated in FIG. 3. Such a device was utilized to stretch the material of the examples below. However, for the examples only one satellite roll with grooves was implemented. A device for stretching such fabrics is described in U.S. Application bearing Attorney Docket Number 19078 PCT, Ser. No. PCT/US03/26247 titled Multiple Impact Device and Method for Treating Flexible Webs, to Robert James Gerndt et al. filed Aug. 22, 2003. Such application is incorporated by reference hereto in its entirety.

The rolls may be constructed of steel or other materials satisfactory for the intended use conditions as will be apparent to those skilled in the art. Also, it is not necessary that the same material be used for all the rolls, and the anvil roll, for example, may be constructed of hard rubber or other more resilient material so as to impart less stressful conditions on the flexible web. Additionally, the rolls may be heated electrically or the rolls may have double shell construction to allow a heating fluid such as a mixture of ethylene glycol and water to be pumped through the roll and provide a heated surface.

As can be seen in FIG. 3, which illustrates a perspective view of a portion of the anvil and satellite grooved roll apparatus of FIG. 1, an anvil roll 42 includes about its periphery a series of grooves in the anvil and satellite rolls 44, 47, and 45 which run concentrically around the roll 42 and, therefore, the web is stretched in the widthwise or cross machine direction. As shown, anvil roll 42 includes grooves and is positioned in working engagement with satellite rolls 44, 47, also having grooves respectively, or alternatively having a smooth surface 45. It will be apparent that the number of engaging rolls and the engagement depth of the respective rolls may be varied, and the rolls may be partially or fully grooved to provide zoned or full stretching along the roll length as desired. The rolls are desirably driven at speeds matched to the desired effective engagement by one or more motors (not shown).

As shown in FIG. 3, the anvil roll 42 is engaged by satellite rolls 44 and 47 which operate to apply a stretching force to the nonwoven layer 10 as it passes through each of the nips formed between the anvil and satellite rolls. In this case, the grooves of one of the satellite rolls extend into mating grooves of the anvil roll to a lesser extent than do the grooves of the other satellite roll. In this manner, stretching forces applied to the nonwoven facing layer 10 may be gradually increased so that there is a reduced tendency to tear or otherwise damage the facing layer and yet stretch to a high degree. It will be apparent that varying the mating engagement of the rolls in this manner may be done with any or all of the satellite rolls and may occur in any order of increasing or decreasing engagement as desired. The term facing layer is used throughout this application as a description of the nonwoven layer since such layer may serve as a facing layer on an absorbent article outer cover. By facing, it is meant that it is the layer facing away from the user of such a product. It should also be noted that similar numbers are used between Figures to designate the same items of previous figures. However, for the purposes of ease of illustration, satellite roll 43 has been removed from FIG. 3.

FIG. 4 is an enlarged partial cross sectional view of an engaged nip, for example, for the embodiment of FIG. 3 showing the path of the facing layer 10 travel. While, for purposes of more clearly illustrating the nip, the path of facing layer 10 is only shown partially across the nip, it will be apparent that the facing layer 10 may and will normally extend completely across the nip. As shown, the grooves 102 of anvil roll 42 intermesh or accommodate the fins (peaks) 110 between the grooves 108 of satellite roll 44. The intermeshing, in this case, maintains spacing, W, between the respective groove walls 112, 114 that is wider than the thickness of the facing layer 10 with the result that the facing layer is generally stretched without being compressed. As shown, H measures the wall height, and E measures the depth of engagement. The number of grooves per inch, N, is measured by counting the number of walls, tip to tip, per inch along the roll, sometimes also called "pitch".

The number of grooves may be varied widely to achieve desired results. For example, for stretching of lightweight nonwoven layers and laminates the number of grooves useful may vary from about 3 to about 15 per inch, although greater or fewer are contemplated. For instance, in one particular embodiment, the number of grooves is between about 5 and 12 grooves per inch. In a further alternative embodiment, the number of grooves is between 5 and 10 per inch. Essentially, in one particular embodiment, the peak to peak distance of the fins, shown as length P in FIG. 4, may be varied from about 0.333 inch to about 0.0666 inch. In an alternative embodiment, the peak to peak distance may be between about 0.200 inch to about 0.083 inch. The engagement of the fins and grooves of the grooved rolls may be from about 0 to 0.300 inch. In an alternative embodiment, the engagement of fins in grooves is between about 0.010 inch to about 0.200 inch. In another embodiment, the engagement may be between about 0.070 inch to about 0.150 inch. Desirably, in one embodiment the total stretch of the material in the CD direction is between about 2.0-2.75× with an engagement of between about 0.100 inch to about 0.150 inch (at about 8 grooves per inch). Such conditions are desirable for a prelamination stretching of a nonwoven material prior to lamination to a film.

For such applications, it may be important that the compression of the material be avoided, and the shape of the intermeshing grooves may be selected for that purpose. Furthermore, the depth of engagement as the grooves intermesh may also be varied so as to achieve the desired stretch level. It is a feature of the present invention that high stretch levels may be attained in localized areas in steps of engagement that avoid single, harsh impact that might damage fragile materials.

In addition to increasing the desired stretch level through increased engagement of the grooved rolls, the effectiveness of the use of grooved rolls can be increased through control of the tension of the nonwoven web as well as by heating the nonwoven web and the grooved rolls. This effectiveness can be seen in the amount of incremental cross-machine direction stretch found when all other parameters are held constant. Tension and heat can be adjusted to provide incremental increases to the overall level of incremental stretch that is imparted to the nonwoven web.

By maintaining machine direction tension of the nonwoven web as the nonwoven web passes through the grooved roll apparatus, the effectiveness of the incremental cross-machine direction stretch is increased. When there is slack in the nonwoven web the web can freely move across its width to some degree. Thus, rather than fully stretching between the ridges of the fins of the grooved rolls, the nonwoven web "slips" between those same ridges. In other words, the width of the nonwoven web decreases as the web "slips" to conform to the contours of the surfaces of the grooved rollers.

When tension is maintained in the machine direction of the nonwoven web, the web will have less ability to "slip" in the cross-machine direction. The tension in the machine direction can be maintained with the use of an S-wrap placed in the web path prior to the grooved roll apparatus and/or through the use of tension unwinds. When tension is maintained the nonwoven web then can be incrementally stretched to a greater degree between the ridges of the fins of the grooved rolls than when the nonwoven web is not held in tension. With higher levels of web tension, the incremental cross-machine stretching will become more effective.

Preheating the nonwoven web prior to entering the grooved roll apparatus and heating the grooved rolls will increase the effectiveness of the grooved rolls in stretching the nonwoven web, and/or the necking process. By heating the nonwoven web and the grooved rolls, the modulus of the web can be reduced and thus increase the ease of incremental cross-machine stretching. The nonwoven web can be heated with the use of a hot air knife or any other similar device as known in the art for heating material webs.

Generally, the nonwoven web will be heated with air that is between about 120° F. to 250° F. Similarly, the grooved rolls are heated to a temperature of between about 120° F. to 250°

F. The necking may be accomplished by an S-roll arrangement (with rolls of differential speeds) immediately following the grooving process.

In making the extensible or stretchable laminate of the present invention, the use of a nonwoven web that has been stretched in the cross-machine direction and then necked to a certain degree, provides for a reduction in cross machine direction tensions in the final product.

To achieve the necking, it is desirable that the ratio of speeds of the stretching rolls/apparatus to necking rolls is between about 0.80 and 0.98, to impart a degree of necking to the nonwoven material of between about 2.5% and 10%. That is the necking rolls will operate at faster speeds than the last stretching roll. In an alternative embodiment, the degree of necking is between about 10 and 40%.

Following necking, the nonwoven web is bonded to a flexible sheet material layer such as a film layer. Bonding may occur through adhesive bonding, such as through slot or spray adhesive systems, thermal bonding or other bonding means, such as ultrasonic, microwave, extrusion coating, and/or compressive force or energy.

An adhesive bonding system 34 is illustrated in FIG. 1. Such a system may be a spray or a slot coat adhesive system. Such slot coat adhesive systems are available from the Nordson Corporation, of Luneburg, Germany. For example, an adhesive applicator die is available from Nordson under the designation BC-62 POROUS COAT model. Such a die may be held on a coating stand such as the NT 1000 series coating stand. It has been found that slot coating adhesive processes provide for more uniform adhesive coverage, over a wide range of adhesive viscosities.

It has also been found that slot coat adhesive processes are desirable methods of bonding as they provide unique attributes over spray adhesive processes. Adhesive is applied to the nonwoven after the nonwoven is grooved and necked. At this point in the process, the grooved nonwoven (FIG. 2) has a corrugated accordion-like surface made up of a series of alternating surface contacting peaks 72 and recessed troughs 74 between the peaks. When spray adhesive is applied to such a grooved nonwoven, the placement of the adhesive is generally uniform throughout the surface of the nonwoven. When such a nonwoven is attached to a polymeric film in a nip the entire surface of the grooved nonwoven, both peaks and troughs, tends to bond with the film. The resulting laminate has a very low level of extensibility and low bulk.

Alternately, when slot coat adhesive processes are used, the adhesive is placed at discrete points on the grooved nonwoven web 10. The adhesive 76 is placed on the peaks 72 of the grooved nonwoven 10 and not in the troughs 74. Generally, a slot coat adhesive process produces a continuous thin film of adhesive. However, when a grooved nonwoven, having peaks and troughs, is passed by the die tip of the slot coat apparatus, the adhesive undergoes a stick-attenuate/break-truncate phenomenon. The adhesive wets and bonds to the peaks of the passing grooved nonwoven web and then is stretched and thinned until the adhesive cohesively fails. The adhesive is broken into discrete portions of adhesive that remain on the peaks of the grooved nonwoven 72. The slot coat adhesive is not applied to the troughs 74 of the grooved nonwoven. When the grooved nonwoven with slot coat adhesive is bonded to a polymeric film, the bonding occurs merely between the film 28 and the discrete points where the grooved nonwoven 10 meets the 28. The extensibility of such a laminate made with slot coat adhesive is greater than that of a similar laminate made with spray adhesive. Because bonding only occurs at discrete points, the grooved nonwoven of the laminate has some amount of free travel, namely the length of nonwoven web between bond points. This free travel allows the laminate to extend at the tension required to extend the film alone for a distance until the grooved nonwoven web is fully extended between the discrete bond points. This allows for a higher extension at lower tensions than current laminates using spray adhesive. This effect is further enhanced with necking and accompanying necking with a facing of an extensible or elastic polymer in the facing. The same effect would be found for a stretchable nonwoven laminate that uses a stretchable (or elastic) film rather than merely an extensible film.

The placement of the adhesive 76 on the discrete peaks 72 of the grooved nonwoven is controllable by optimizing the adhesive characteristics, adhesive temperature, amount of adhesive used, nip pressure and degree of processing of the grooved nonwoven. The slot coat process will tend to place the adhesive on the peaks of the grooved laminate but controlling the adhesive by these variables will insure that the adhesive will stay primarily on the peaks throughout processing of the laminate. The optimized adhesive will have optimized characteristics, including melt temperature, rheology, and open time, such that adhesive will stay placed on the peaks rather than flow from the peaks and into the troughs of the grooved nonwoven.

The nip pressure used to laminate the grooved nonwoven 10 with slot coat adhesive to the polymeric film 28 will also determine the ability to bond in only discrete points. If too much nip pressure is used, the adhesive will be squeezed from the peaks of the grooved nonwoven through the nonwoven and into the troughs of the same nonwoven. The higher the nip pressure, the greater degree that adhesive will be forced from the peaks of the grooved nonwoven to other portions of the grooved nonwoven. Alternately, if too little nip pressure is used there can be inadequate bonding between the polymeric film and the grooved nonwoven. Lower nip pressure can be balanced by adhesive formulation with higher tackiness.

In a similar way the degree of processing will also affect the placement of the adhesive. When the grooved nonwoven and/or laminate undergo a higher degree of processing before the adhesive has fully set, the adhesive will be caused to flow from its placement on the peaks. Again the formulation of the adhesive can be balanced against the degree of processing by providing a formulation that will set up to an appropriate level relative to the processing being used. This would likely require an adhesive that has a shorter open time when dealing with higher machine speeds or more tortuous machine paths for the laminate.

The adhesive used in the slot coat embodiment of the present invention must be suitable for slot coat adhesive processes and must be able to bond the flexible sheet materials. It is also desired that the adhesive maintain the bond when the laminate is extended or stretched in use. Examples of suitable adhesives that may be used in the practice of the invention include Rextac 2730 and 2723 available from Huntsman Polymers of Houston, Tex., as well as adhesives available from Bostik Findley, Inc, of Wauwatosa, Wis., such as H9375-01. Desirably, adhesive is applied at a basis weight of between about 1 and 3 gsm.

Following lamination of the nonwoven layer to the film the laminate is desirably allowed to retract between about 10 and 30 percent in order to achieve some machine direction stretch in the laminate as well. Such retraction may be accomplished by a temperature controlled section of the process. For example, the material may be run across several rolls with two rolls being heated to about 180 degrees F. and two of them being chilled to about 60 degrees F. The heating rolls would be followed by the chilling rolls and any number of rolls may be implemented for this purpose. The film layer is desirably bonded to the nonwoven in the nip while the film is in a partially relaxed condition in order to achieve some machine direction retraction.

It has been recognized that the more continuous the layer of adhesive applied to such nonwoven facing layer prior to lamination, the higher the level of tension encountered in the cross-machine direction, and particularly for first cycle elongation tension as discussed below. The first cycle elongation tension is the tension encountered during the stretch of a laminate on a first instance or cycle. While the tension normally reduces following this first extension, it would be desirable to reduce the overall first cycle tension encountered to the extent possible, so as to enhance a material's ability to be easily stretched and to provide improved engageability for hook fasteners, improved fit and/or ease of donning. It has been found that the more tension that a material demonstrates at first stretch, the more likely it will be that the material will pose difficulty for a child to put on a product containing the material in use.

As still another alternative to the adhesive lamination arrangement previously described, the adhesive is deposited as a parallel array of machine direction oriented adhesive filaments along the peaks of the nonwoven facing layer at 76. Such filaments would allow for the free migration of fibers in an extensible nonwoven facing layer. Such migration of fibers, (not being held in place by traditional slot coatings) would translate into lower first cycle extension tensions. Such lower tensions would allow for lower tensions when donning garments that incorporate such materials. Such method allows for maximum cross-machine direction extension, while still providing for adequate lamination.

In still a further alternative embodiment, the comparably lower cross-machine direction tension laminates may be further modified in a post lamination, post winding process to further reduce tensions encountered on a first elongation cycle. For example, as the laminate material is unwound for converting into an absorbent product, the laminate material can be cycled (stretched) in the cross-machine direction to imitate the stress that such material would encounter during use. However, such first stretch would only disrupt minor adhesive bonds (such as some of those resulting from slot-coating applications) and would create non-recoverable deformations in the film that would normally occur during the product's first use by a consumer. Such stretch/cycling can be achieved by the use of edge pinners, tenter frames or bowed spreader bars. Such cycling would not degrade the in-use elongation and retraction properties, but would merely lower the tension to achieve such stress on the first in-use cycle. See in this regard, U.S. Patent Publication 2004/0121687, which is hereby incorporated by reference in its entirety.

The inventive film laminate may be incorporated into numerous personal care products. For instance, such material is particularly advantageous as a stretchable outer cover for various personal care products. Additionally, such film laminate may be incorporated as a base fabric material in protective garments such as surgical or hospital drapes. In still a further alternative embodiment, such material may serve as base fabric for protective recreational covers such as car covers and the like.

Figure 5:
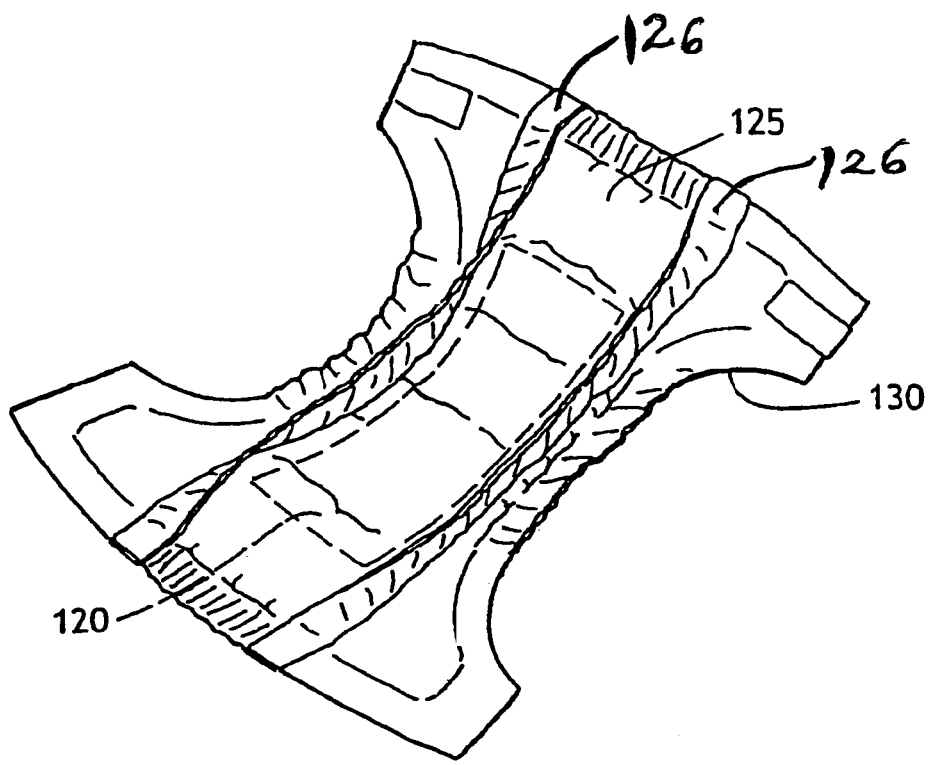
FIG. 5 is an illustration of a diaper made in accordance with the invention.

In this regard, FIG. 5 is a perspective view of an absorbent article, such as a disposable diaper of the present invention in its opened state. The surface of the diaper which contacts the wearer is facing the viewer. With reference to FIG. 5, the disposable diaper generally defines a front waist section, a rear waist section, and an intermediate section which interconnects the front and rear waist sections. The front and rear waist sections include the general portions of the article which are constructed to extend substantially over the wearer's front and rear abdominal regions, respectively, during use. The intermediate section of the article includes the general portion of the article that is constructed to extend through the wearer's crotch region between the legs.

The absorbent article includes an outer cover 130, a liquid permeable bodyside liner 125 positioned in facing relation with the outer cover, and an absorbent body 120, such as an absorbent pad, which is located between the outer cover and the bodyside liner. Containment flaps 126 are also positioned adjacent each side of the central liner area for containing waste. The outer cover in the illustrated embodiment coincides with the length and width of the diaper. The absorbent body generally defines a length and width that are less than the length and width of the outer cover, respectively. Thus, marginal portions of the diaper, such as marginal sections of the outer cover, may extend past the terminal edges of the absorbent body. In the illustrated embodiment, for example, the outer cover extends outwardly beyond the terminal marginal edges of the absorbent body to form side margins and end margins of the diaper. The bodyside is generally coextensive with the outer cover but may optionally cover an area which is larger or smaller than the area of the outer cover, as desired.

The outercover (or backsheet as it is sometimes called) and bodyside liner are intended to face the garment and body of the wearer, respectively, while in use. The film laminate of the present invention may conveniently serve as the outercover in such an article, providing a barrier, an aesthetically pleasing appearance and a pleasant tactile touch. The film layer of the laminate 28 would desirably face the skin of the product's user while the nonwoven layer 10 faces away from the skin of the products' user. Such a laminate may also serve as material for the containment flaps 126.

Fastening means, such as hook and loop fasteners, may be employed to secure the diaper on a wearer. Alternatively, other fastening means, such as buttons, pins, snaps, adhesive tape fasteners, cohesives, mushroom-and-loop fasteners, or the like, may be employed. In this regard, the inventive material may be used as the loop material as part of a stretchable (elastic) or extensible outercover.

The various components of the diaper are integrally, assembled together employing various types of suitable attachment means, such as adhesive, sonic bonds, thermal bonds or combinations thereof. In the shown embodiment, for example, the bodyside liner and outercover may be assembled to each other and to the absorbent body with lines of adhesive, such as a hotmelt, pressure-sensitive adhesive. Similarly, other diaper components, such as elastic members and fastening members may be assembled into the article by employing the above-identified attachment mechanisms. The article of the invention desirably includes the film laminate as a stretchable outer cover which encompasses a stretchable fabric layer which is operatively attached or otherwise joined to extend over a major portion of the outward surface of the article. In regions where the stretchable outercover is not affixed to non-stretchable portions of the article or otherwise restricted from extending, the stretchable outercover can be free to advantageously expand with minimal force. In desired aspects, the outercover can be stretchable along the longitudinal direction, lateral direction, or along a combination of both the lateral and longitudinal directions. In particular, it is desirable that the portion of the stretchable outer cover located in the waist sections are capable of extending in the lateral direction to provide improved fastening of the article about the wearer and improved coverage of the hips and buttocks of the wearer particularly in the rear waist section and enhanced breathability in the waist sections. For example, if the fasteners and or side panels are located along the side edges in the rear waist section of the diaper, at least a portion of the outercover in the rear waist section will desirably extend to provide enhanced coverage over the buttocks of the wearer in use for improved containment and aesthetics.

Moreover, it is also desirable that at least portions of the stretchable outercover located over the absorbent body can extend during use for improved containment. For example, as the absorbent body absorbs fluid exudates and expands outwardly, the stretchable outer cover can readily elongate and extend in correspondence with the expansion of the absorbent body and/or other components of the article to provide void volume to more effectively contain the exudates. The stretchable outer cover of the present invention is desirably capable of providing a selected stretch when subjected to an applied tensile force, and the ability to retract upon removal of such applied force.

Figure 6:
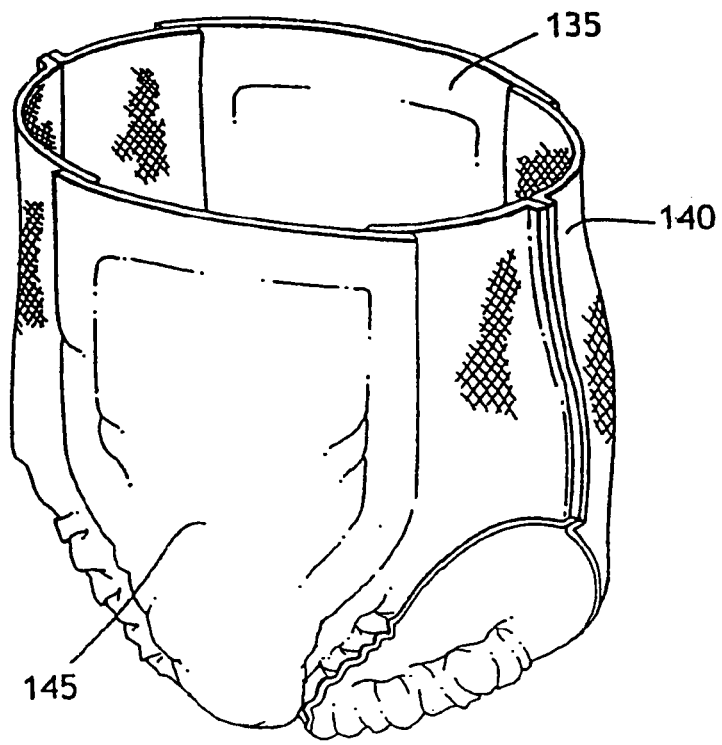
FIG. 6 is an illustration of a training pant made in accordance with the invention.
Figure 7:
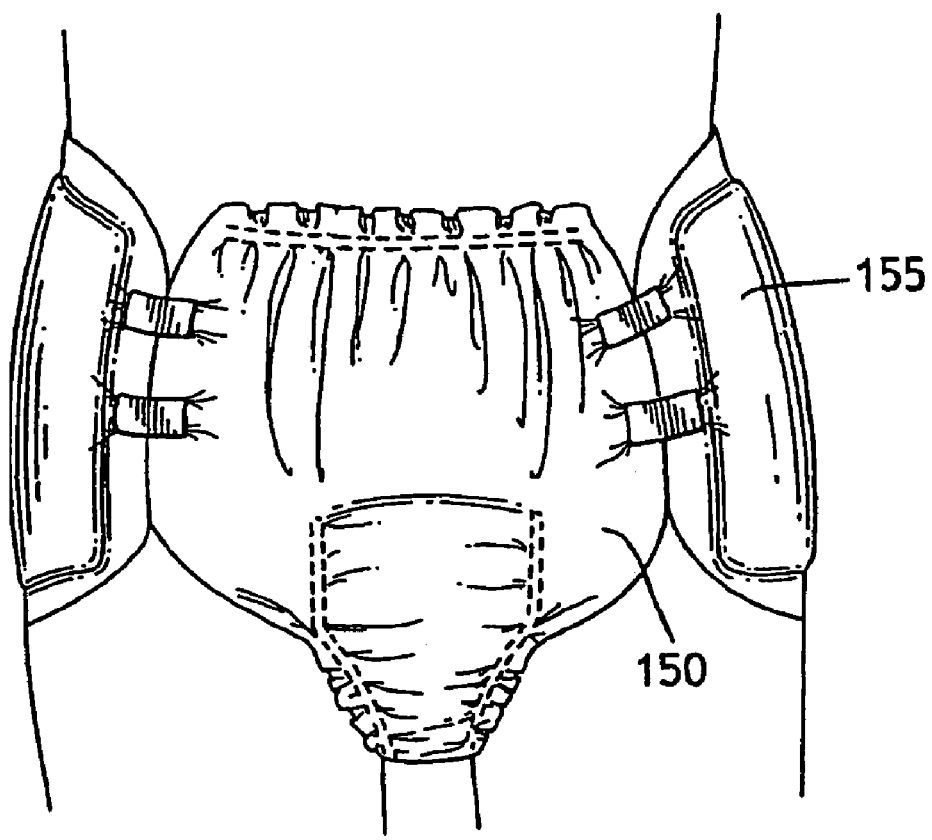
FIG. 7 is an illustration of an absorbent underpant made in accordance with the invention.
Figure 8:
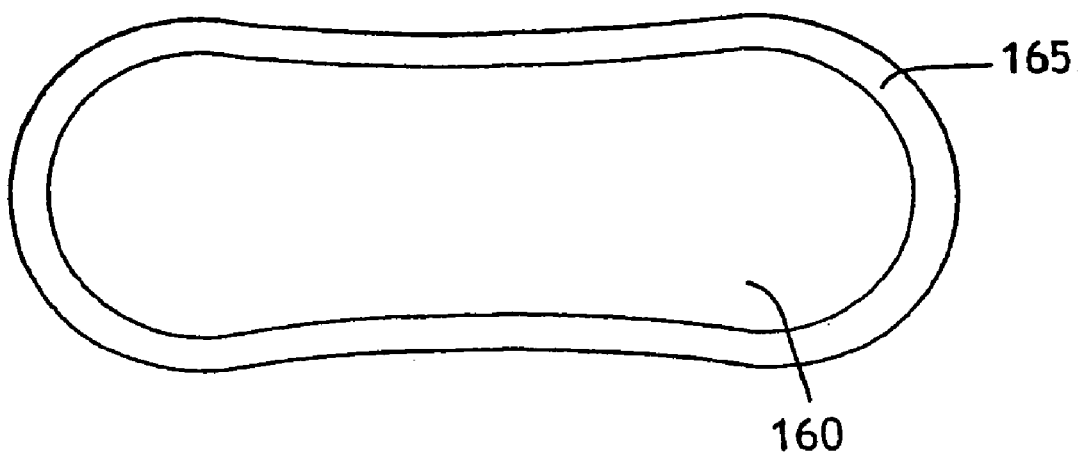
FIG. 8 is an illustration of a feminine hygiene product made in accordance with the invention.
Figure 9:
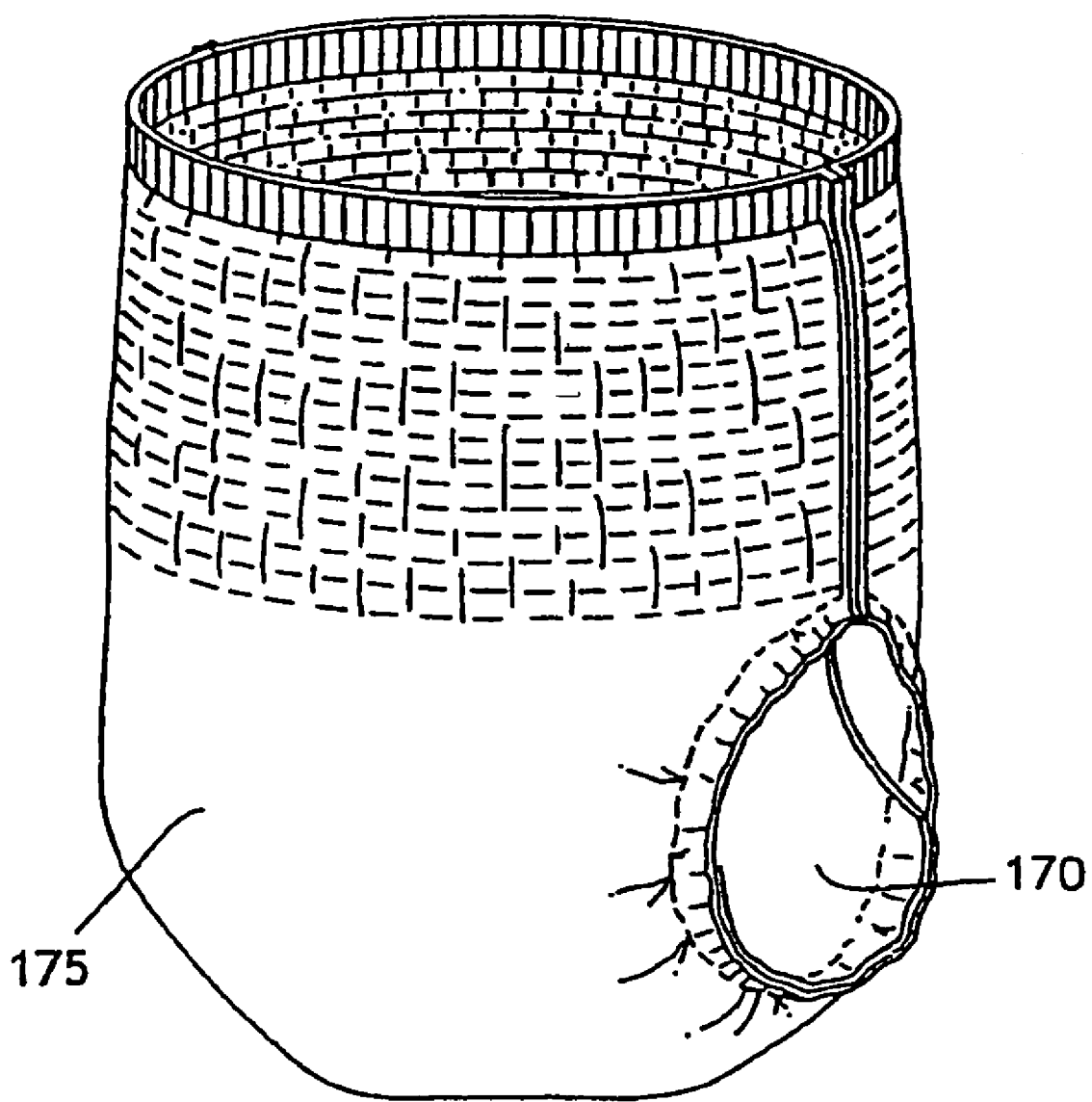
FIG. 9 is an illustration of an adult incontinence product made in accordance with the invention.

As can be seen in the various other absorbent personal care product embodiments, the inventive material may be used as an "outer cover" in a variety of product applications including a training pant, underpant, feminine care product, and adult incontinence product. For instance, as can be seen in FIG. 6, the distinctive film laminate can serve as the outercover on both the back 135 and front portions of a training pant, separated by distinct elastic side panels 140. Alternatively, the inventive material can serve as a continuous full outercover on the front and back, as well as the side panel areas (as elastic side panels). As can be seen in FIG. 7, the distinctive film laminate can serve as an outercover in an underpant, such as either 150 or 155. As can be seen in FIG. 8, the distinctive film laminate can serve as an outercover/backsheet 165 in a feminine care pantiliner 160. As can be seen in FIG. 9, the distinctive film laminate can serve in an adult incontinence product as an outercover 175. Additionally such film laminate may serve as a sanitary napkin coversheet or a diaper liner, or further processed such as by being apertured and the like, before being used as base materials in such products or product applications.

The invention will be illustrated by examples which are representative only and not intended to limit the invention which is defined by the appended claims and equivalents. Modifications and alternatives will be apparent to those skilled in the art and are intended to be embraced by the invention as claimed.

EXAMPLES

The examples were carried out with equipment under the following conditions unless stated otherwise in the examples:

Conditions

Several fibrous facing layers were utilized in this evaluation, including polyolefinic fibers from BBA Fiberweb of Simpsonville, S.C., under the designation SOFSPAN 120 and fibers incorporating developmental propylene-ethylene copolymers obtained from The Dow Chemical Company.

A fibrous nonwoven web was generally unwounded with a 9.5 psi unwind tension and then introduced into a nip of intermeshing grooved steel rolls (of a satellite grooved roll arrangement) at a velocity of 99 meters/min (325 ft/min). Each roll had a width (end to end) of about 66 cm (26") with the diameter of the satellite groove rolls about 27 cm (10.6") and the diameter of the main center groove roll about 45 cm (17.85"). Each groove was formed with a depth of 0.39 cm (0.154") and with a peak to peak distance of 0.31 cm (0.125") resulting in a maximum draw ratio of approximately 2.8×.

The engagement of the grooved roll was set for each code to obtain the desired level of incremental stretch.

The fibrous nonwoven web was heated by a hot air knife set at a specific temperature (of 93° C. (200° F.) for webs from BBA and about 65.6° C. (150° F.) for webs which incorporated propylene-ethylene polymers) while it passed by hot air knife and the two temperature controlled nips between grooved rolls.

Lamination to film and nonwoven layers was accomplished using adhesive lamination with a Nordson BC-62 Porous Coat slot coat adhesive system, as produced by the Nordson Corporation of Dawsonville, Ga. Findley adhesive H9375-01, produced by Bostik Findley Inc. of Wauwautosa, Wis., was melted to a temperature of 177° C. (350° F.) and applied to the spunbond sheet at the noted add-on levels. The stretched spunbond web and film were then joined together by a laminating nip and using a nip pressure of 2 PLI and 5% draw at the upper roll to maintain the spunbond dimension stability at the time of lamination with the film.

Examples of Materials Made Utilizing CD Stretching Followed by Specific Levels of Nonwoven Necking Specific Examples Code 1 A 50/50 blend of Resin P-E3 and PP 3155 (polypropylene) of Exxon Mobil as the facing layer with styrenic block copolymer film without skin layer. Resin P-E 3 is a developmental propylene-ethylene copolymer obtained from The Dow Chemical Company containing 12 percent by weight units derived from ethylene and having a melt flow rate of 25 g/10 min. This copolymer exhibits a heat of fusion of 17.4 Joules/gram, which corresponds to a crystallinity of 11 wt %, and a MWD of 3. This propylene-ethylene copolymer exhibits triad isotacticity (mm) of 0.96.

A film/nonwoven laminate was produced. The film layer filler concentrate was comprised of 75% calcium carbonate which was dispersed into a polymeric carrier resin. The calcium carbonate, available from Omya, Inc. North America of Proctor, Vt., and designated as 2SST, has an average particle size of 2 microns with a top cut of 8-10 microns and a coating of approximately 1% stearic acid. The polymeric carrier resin which comprises 25% of the blend was a DOWLEX™ 2517 LLDPE resin supplied by The Dow Chemical Company of Midland Mich. DOWLEX 2517™ resin has a density of 0.917 g/cc and a melt index of 25. The 75/25 blend of calcium carbonate and LLDPE resin was subsequently blended with 33% of SEPTON 2004 which is a SEPS based styrenic block copolymer to provide a final calcium carbonate concentration of 50.25% by weight. The SEPTON resin is available from Septon Company of America of Pasadena, Tex. Similar film manufacture was described in U.S. patent application Ser. No. 10/703761, filed Nov. 7, 2003, which is incorporated by reference herein in its entirety.

The formulation was formed into a film by casting onto a chill roll set to 37.8° C. (100° F.) at an unstretched basis weight of approximately 67 gsm. The casting speed was 140 ft/minute. The film was heated to a temperature of 51.7° C. (125° F.), stretched 3.5 times its original length using a machine direction orientor at a line speed of 494 ft/minute. The film was not retracted but passed across multiple rolls at temperature of 21.1° C. (70° F.) to a line speed of 494 feet per minute resulting in a stretched basis weight of approximately 33 gsm (film both MD and CD elastic).

The fibrous nonwoven web was a 20 gsm (0.6 osy) spunbond web produced with a blend of 50 weight percent P-E3 copolymer/50 weight percent Exxon Mobil 3155 Polypropylene. The fibrous nonwoven web was introduced into a nip of intermeshing grooved steel rolls at a velocity of 473 ft/minute, as generally illustrated in FIG. 4 with the grooves in the rolls being concentric. Each groove was formed with a depth of 0.51 cm (0.200") and with a peak to peak distance of 0.31 cm (0.125") resulting in a maximum draw ratio of 3.4x. In this sample the spunbond was stretched to a draw of about 2.0× in the cross machine direction (CD). The fibrous nonwoven web was heated with a hot air knife set at 65.6° C. (150° F.) and then passed through the temperature controlled nip between grooved rolls to intermeshing engagement of 2.794 mm (0.110"). The spunbond was drawn 4% in the machine direction between the groove roll unit and the lamination unit causing the CD width to be necked in 33.8% (even though it had been stretched in the CD by the grooved rolls) to a new width of 11.25 inches, which was less than the starting width (prior to being run through the groove rolls) of the web of 17.0 inches. The width was for the accordion shaped web, as opposed to the flattened web.

Lamination of the film and nonwoven layer was accomplished using adhesive lamination with a slot die coater. H9375-01 adhesive, produced by Bostik Findley, was melted to a temperature of 177° C. (350° F.) and applied to the spunbond sheet with an add-on level of about 1.0 gsm and a nip pressure of 2 pounds per linear inch.

The produced laminate was retracted 15% in the machine direction between the lamination unit and a fourth roll in the annealing unit maintaining its width. The laminate was annealed and cooled using 4 temperature controlled rolls. The laminate with the film side in contact with the rolls was heated at 82° C. (180° F.) over two rolls and then cooled at 16° C. (60° F.) over the next two rolls to set the final machine and cross machine direction stretch material properties. Finally the laminate was transferred with minimal retraction to the winder. The resulting tension measured within an hour of making the material was 398 gf at 50% extension in the cross machine direction and 859 gf at 30% extension in the machine direction.

Code 2 Facing layer of BBA SOFSPAN 120 and film without skin layer.

A film/nonwoven laminate was produced. The film layer filler concentrate was comprised of 75% calcium carbonate which was dispersed into a polymeric carrier resin. The calcium carbonate, available from Omya, Inc. North America of Proctor, Vt., and designated as 2SST, has an average particle size of 2 microns with a top cut of 8-10 microns and a coating of approximately 1% stearic acid. The polymeric carrier resin which comprises 25% of the blend was a DOWLEX™ 2517 LLDPE resin supplied by The Dow Chemical Company of Midland Mich. The 75/25 blend of calcium carbonate and LLDPE resin was subsequently blended with 33% of SEPTON 2004 to provide a final calcium carbonate concentration of 50.25% by weight.

The formulation was formed into a film by casting onto a chill roll set to 100° F. at an unstretched basis weight of approximately 63 gsm. The casting speed was 124 ft/minute. The film was heated to a temperature of 51.7° C. (125° F.), stretched 4.0 times its original length using a machine direction orientor at a line speed of 493 feet per minute. The film was not retracted but passed across multiple rolls at a temperature of 21.1° C. (70° F.) to a line speed of 493 feet per minute resulting in a stretched basis weight of approximately 32.7 gsm (both a CD and MD elastic film).

The fibrous nonwoven web was a 20 gsm (0.6 osy) spunbond web produced by BBA with the designation of SOFSPAN 120. The fibrous nonwoven web was introduced into a nip of intermeshing grooved steel rolls at a velocity of 482 ft/minute as described in the previous example. In this sample the spunbond was stretched to a draw of 2.6× in the cross machine direction (CD). The fibrous nonwoven web was heated to a temperature of 93.3° C. (200° F.) while it passed subsequently under a hot air knife and through the temperature controlled nip between grooved rolls to intermeshing engagement of 3.810 mm (0.150"). The spunbond was drawn 1% in the machine direction between the groove roll unit and the lamination unit causing the CD width to be necked in 3.6% (even though it had been stretched in the CD by the grooved rolls) to a new width of 20.25 inches, which was less than the starting width (prior to being run through the groove rolls) of the web of 21.0 inches.

Lamination of the film and nonwoven layer was accomplished using adhesive lamination with a slot die coater. H9375-01 adhesive was melted to a temperature of 177° C. (350° F.) and applied to the spunbond sheet with an add-on level of 1.0 gsm and a nip pressure of 2 pounds per linear inch.

The produced laminate was retracted 10% in the machine direction between the lamination unit and a fourth roll in an annealing unit maintaining its width. The laminate was annealed and cooled using 4 temperature controlled rolls. The laminate with the film side in contact with the rolls was heated at 82° C. (180° F.) over two rolls and then cooled at 16° C. (60° F.) over the next two rolls to set the final machine and cross machine direction stretch material properties. Finally the laminate was transferred with minimal retraction to the winder. The resulting tension measured within an hour of making the material was 250 gf at 50% extension in the cross machine direction and 600 gf at 30% extension in the machine direction.

Code 3 A facing layer of BBA SOFSPAN 120 with film having skin layer (Biaxially Stretchable and Recoverable).

A film/nonwoven laminate was produced. The film layer filler concentrate was comprised of 75% calcium carbonate which was dispersed into a polymeric carrier resin. The calcium carbonate, available from Omya, Inc. North America of Proctor, Vt., and designated as 2SST, has an average particle size of 2 microns with a top cut of 8-10 microns and a coating of approximately 1% stearic acid. The polymeric carrier resin which comprises 25% of the blend was a DOWLEX™ 2517 LLDPE resin. The 75/25 blend of calcium carbonate and LLDPE resin was subsequently blended with 33% of SEPTON 2004 to provide a final calcium carbonate concentration of 50.25% by weight. A 1.5% by volume skin layer of LD202.48, from Exxon Mobil which is a LDPE, was applied to the surface opposite of the spunbond.

The formulation was formed into a film by casting onto a chill roll set to 120° F. at an unstretched basis weight of approximately 60.5 gsm. The casting speed was 169 ft/minute. The film was heated to a temperature of 51.7° C. (125° F.), stretched 3.1 times its original length using a machine direction orientor at a line speed of 523 feet per minute. The film was then retracted 21% resulting in a stretched basis weight of approximately 31.5 gsm. The film was retracted across multiple rolls at temperature of 21.1° C. (70° F.) to a line speed of 415 feet per minute.

The fibrous nonwoven web was a 20 gsm (0.6 osy) spunbond web produced by BBA with the trade name of SOFSPAN 120. The fibrous nonwoven web was introduced into a nip of intermeshing grooved steel rolls at a velocity of 394 ft/m. Each groove was formed with a depth of 0.51 cm (0.200") and with a peak to peak distance of 0.31 cm (0.125"). In this sample the spunbond was stretched to a draw of 2.6× in the cross machine direction (CD). The fibrous nonwoven web was heated to a temperature of 93.3° C. (200° F.) while it passed subsequently under a hot air knife and through the temperature controlled nip between grooved rolls to intermeshing engagement of 3.810 mm (0.150"). The spunbond was drawn 5% in the machine direction between the groove roll unit and the lamination unit causing the CD width to be necked in 4.5% (even though it had been stretched in the CD by the grooved rolls) to a new width of 21.0 inches, which was less than the starting width (prior to being run through the groove rolls) of the web of 22.0 inches. Again, as in the previous examples, the third width, of 21 inches was of the accordion shaped nonwoven.

Lamination of the film and nonwoven layer was accomplished using adhesive lamination with a slot die coater. H9375-01 adhesive was melted to a temperature of 177° C. (350° F.) and applied to the spunbond sheet with an add-on level of 1.0 gsm and a nip pressure of 2 pounds per linear inch.

The produced laminate was retracted 18% in the machine direction between the lamination unit and a fourth roll in the annealing unit maintaining its width. The laminate was annealed and cooled using the 4 temperature controlled rolls. The laminate with the film side in contact with the rolls was heated at 82° C. (180° F.) over two rolls and then cooled at 16° C. (60° F.) over the next two rolls to set the final machine and cross machine direction stretch material properties. Finally the laminate was transferred with minimal retraction to the winder. The resulting tension measured within an hour of making the material was 378 gf at 50% extension in the cross machine direction and 864 gf at 30% extension in the machine direction. It should be recognized that in the example involving a skin layer, the skin layer is extruded together with the styrenic layer as one sheet material.

Code 4 Uniaxially Stretchable and Recoverable (CD Direction Only)

A film/nonwoven laminate was produced. The film layer filler concentrate was comprised of 75% calcium carbonate which was dispersed into a polymeric carrier resin. The calcium carbonate, available from Omya, Inc. North America of Proctor, Vt., and designated as 2SST, has an average particle size of 2 microns with a top cut of 8-10 microns and a coating of approximately 1% stearic acid. The polymeric carrier resin which comprises 25% of the blend was a DOWLEX™ 2517 LLDPE resin. The 75/25 blend of calcium carbonate and LLDPE resin was subsequently blended with 33% of SEPTON 2004 to provide a final calcium carbonate concentration of 50.25% by weight. A 1.5% volume skin layer of LD202.48 was applied to the surface of the film opposite of the spunbond. It should be recognized that in the example involving a skin layer, the skin layer is extruded together with the styrenic layer as one sheet material.

The formulation was formed into a film by casting onto a chill roll set to 120° F. at an unstretched basis weight of approximately 60.5 gsm. The casting speed was 169 ft/minute. The film was heated to a temperature of 125° F., stretched 3.1 times its original length using a machine direction orientor at a line speed of 523 feet per minute. The film was retracted 21% resulting in a stretched basis weight of approximately 31.5 gsm. The film was then retracted and annealed across multiple rolls at temperature of 65.6° C. (150° F.) to a line speed of 415 feet per minute. It should be recognized that when film layers in examples are annealed before lamination, the film layers are CD elastic only, whereas if no annealing is described for a particular example, the film is both CD and MD elastic (biaxially stretchable). All of the films in the examples are also breathable in that they demonstrate greater than 100 g/m²/24 hours as measured using a Mocon-type test method as previously described.

The fibrous nonwoven web was a 20 gsm (0.6 osy) spunbond web with 20 weight percent P-E3 and 80 weight percent Exxon Mobil 3155 Polypropylene. The fibrous nonwoven web was introduced into a nip of intermeshing-grooved steel rolls at a velocity of 352 ft/m as described for the previous examples. Each groove was formed with a depth of 0.51 cm (0.200") and with a peak to peak distance of 0.31 cm (0.125") resulting in a maximum draw ratio of 3.4×. In this sample the spunbond was stretched to a draw of 1.75× in the cross machine direction (CD). The fibrous nonwoven web was heated to a temperature of 65.6° C. (150° F.) while it passed subsequently under a hot air knife and through the temperature controlled nip between grooved rolls to intermeshing engagement of 2.286 mm (0.090"). The spunbond was drawn 15% in the machine direction between the groove roll unit and the lamination unit causing the CD width to be necked in 33.3% (even though it had been stretched in the CD by the grooved rolls) to a new width of 18.0 inches, which was less than the starting width (prior to being run through the groove rolls) of the web of 27.0 inches.

Lamination of the film and nonwoven layer was accomplished using adhesive lamination with a slot die coater. H9375-01 adhesive, was melted to a temperature of 177° C. (350° F.) and applied to the spunbond sheet with an add-on level of 1.5 gsm and a nip pressure of 2 pounds per linear inch.

The laminate was annealed and cooled using 4 temperature controlled rolls. The laminate with the film side in contact with the rolls was heated at 82° C. (180° F.) over two rolls and then cooled at 16° C. (60° F.) over the next two rolls to set the final machine and cross machine direction stretch material properties. Finally the laminate was transferred with minimal retraction to the winder. The resulting tension measured within an hour of making the material was 471 gf at 50% extension in the cross machine direction. There was no stretch in the machine direction and was not tested.

Code 5—Comparison to previous Code but Necked Only

A film/nonwoven laminate was produced. The film layer filler concentrate was comprised of 75% calcium carbonate which was dispersed into a polymeric carrier resin. The calcium carbonate, available from Omya, Inc. North America of Proctor, Vt., and designated as 2SST, has an average particle size of 2 microns with a top cut of 8-10 microns and a coating of approximately 1% stearic acid. The polymeric carrier resin which comprises 25% of the blend was a DOWLEX™ 2517 LLDPE resin. The 75/25 blend of calcium carbonate and LLDPE resin was subsequently blended with 33% of SEPTON 2004 to provide a final calcium carbonate concentration of 50.25% by weight. A 1.5% skin layer of LD202.48 was applied to the surface opposite of the spunbond.

The formulation was formed into a film by casting onto a chill roll set to 120° F. at an unstretched basis weight of approximately 60.5 gsm. The casting speed was 169 ft/minute. The film was heated to a temperature of 125° F., stretched 3.1 times its original length using a machine direction orientor at a line speed of 523 feet per minute. The film was then retracted 21% and annealed resulting in a stretched basis weight of approximately 31.5 gsm. The film was retracted and annealed across multiple rolls at temperature of 65.6° C. (150° F.) to a line speed of 415 feet per minute.

The fibrous nonwoven web was a 20 gsm (0.6 osy) spunbond web with 20 weight percent P-E3 and 80 weight percent Exxon Mobil 3155 Polypropylene. The fibrous nonwoven web was put through a rubber roll S-wrap. The fibrous nonwoven web was heated to a temperature of 65.6° C. (150° F.)

while it passed subsequently under a hot air knife. The spunbond was drawn 15% in the machine direction between the groove roll unit and the lamination unit causing the CD width to be necked in 42.6% to a new width of 15.5 inches, which was less than the starting width of the web of 27.0 inches. It should be noted that the nips of the groove roll unit were open and the web was necked between the last roll, 45 (which was a smooth rubber roll) and the adhesive nip 36.

Lamination of the film and nonwoven layer was accomplished using adhesive lamination with a slot die coater. H9375-01 adhesive was melted to a temperature of 177° C. (350° F.) and applied to the spunbond sheet with an add-on level of 1.5 gsm and a nip pressure of 2 pounds per linear inch.

The laminate was annealed and cooled using 4 temperature controlled rolls. The laminate with the film side in contact with the rolls was heated at 82° C. (180° F.) over two rolls and then cooled at 16° C. (60° F.) over the next two rolls to set the final machine and cross machine direction stretch material properties. Finally the laminate was transferred with minimal retraction to the winder. The resulting tension measured within an hour of making the material was 655 gf at 50% extension in the cross machine direction. There was no stretch in the machine direction and was not tested.

Figure 10:
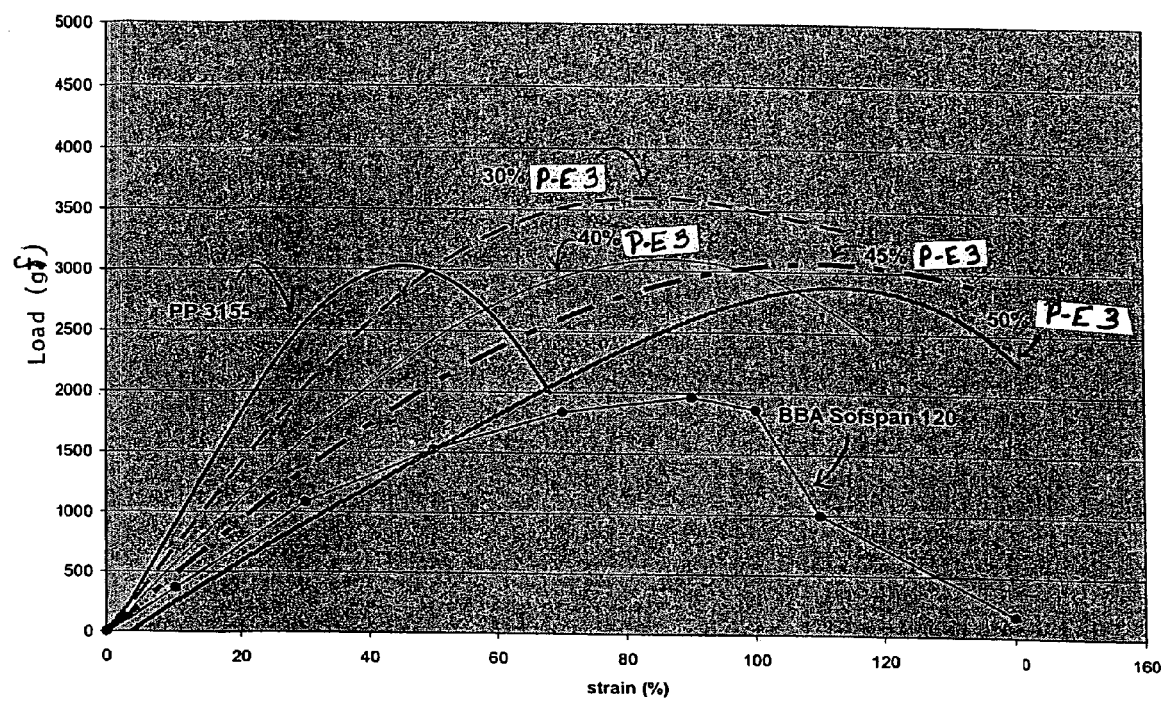
FIG. 10 is a graph illustrating the properties of various facing layers for the inventive laminate.

In order to demonstrate the effectiveness of using various nonwoven facing layers for the inventive method, various materials including polypropylene, polypropylene-ethylene copolymers and blends in nonwoven facing layers were evaluated using a stress/strain analysis. The graph in FIG. 10 illustrates CD load versus strain for the various facing materials at 0.6 osy. The graph provides a comparison for determining how much a nonwoven spunbond facing layer can be stretched in the CD without shredding the layer. A facing layer with load/strain values approaching the slope of the BBA material, and having similar peak elongation, is capable of being drawn 2.6 times, while that near the slope of the 3155 material is less likely to be capable of such drawing. A variety of materials were therefore identified which demonstrated particular resistance to shredding via the grooved roll stretching process, and which also demonstrated both a desirable level of softness and performance as part of an elastic laminate. Such facings offer extensibility, durability, tactile appeal and fastening capability. The stress strain behavior of such facings offer both extension at low load (in process and post process).

While the invention has been described in detail with reference to specific embodiments thereof, it should be understood that many modifications, additions and deletions can be made thereto without departure from the spirit and scope of the invention as set forth in the following claims.

We claim:

1. A laminate material made by:
   a. providing a first flexible sheet material;
   b. providing a second flexible sheet material having a first surface and a second surface, and also having a first width of 1×;
   c. stretching said second flexible sheet material in a cross-machine direction to a second flattened width of between about 1.2× and 3×;
   d. necking said second flexible sheet material to create an accordion shaped material, thereby reducing the second width of the sheet material to a third width less than the width of the first width such that said third width is between 0.60× to 0.975× when in an accordion configuration;
   e. applying adhesive to said first surface of said second flexible sheet material with a slot coat adhesive process; and
   f. joining the first flexible sheet material to the first surface of the second flexible sheet material;
   wherein adhesive will stay primarily on the peaks of the accordion shaped second flexible sheet material.

2. A laminate material of claim 1 wherein said laminate is either uniaxial or biaxial elastic and demonstrates a cross-machine direction tension between about 200 and 750 gf at 50 percent extension, with a machine direction tension between 500 and 1000 gf at 30 percent extension.

3. A laminate material of claim 2 wherein said laminate is either uniaxial or biaxial elastic and demonstrates a cross-machine direction tension between about 200 and 450 gf at 50 percent extension, with a machine direction tension between 500 and 1000 gf at 30 percent extension.

4. A personal care article made with the material of claim 1.

5. A personal care article having an outercover, wherein said outercover comprises the material of claim 1.

6. A laminate material of a first flexible layer and a second flexible layer, wherein said laminate is either uniaxial or biaxial elastic and demonstrates a cross-machine direction tension between about 200 and 750 gf at 50 percent extension, with a machine direction tension between 500 and 1000 gf at 30 percent extension.

7. A laminate material of a first flexible layer and a second flexible layer, wherein said laminate is either uniaxial or biaxial elastic and demonstrates a cross-machine direction tension between about 200 and 450 gf at 50 percent extension, with a machine direction tension between 500 and 1000 gf at 30 percent extension.

8. A laminate material of claim 1 wherein said laminate demonstrates a cross-machine direction tension between about 200 and 600 gf at 50 percent extension.

9. A laminate material of claim 1 wherein said laminate demonstrates a cross-machine direction tension between about 200 and 450 gf at 50 percent extension.

10. A personal care article of claim 4, wherein the article is one of a diaper, a training pant, an absorbent underpant, a feminine hygiene product, and an adult incontinence product.

11. A personal care article of claim 4, wherein said article is configured so that said first flexible sheet material faces the skin of the article's user when in use for the article's intended purpose.

12. A personal care article of claim 4, wherein said laminate serves as material for containment flaps.

13. A personal care article of claim 4, wherein said laminate serves as loop material.

14. A personal care article of claim 4, wherein said laminate is apertured.

15. A personal care article of claim 4, wherein the article is a diaper and said laminate serves as a diaper liner.

16. A personal care article of claim 4, wherein the article is a sanitary napkin and said laminate serves as a coversheet.

17. A laminate material, comprising:
    a first flexible, elastic sheet material;
    a second flexible sheet material having a first surface and a second surface, the second flexible sheet material being an accordion shaped material with a plurality of peaks defining said first surface; and
    the first flexible, elastic sheet material being joined by adhesive to the first surface of the second flexible sheet material wherein the adhesive is primarily on the peaks of the accordion shaped second flexible sheet material.

* * * * *